US009945786B2

(12) United States Patent
Kilfeather et al.

(10) Patent No.: US 9,945,786 B2
(45) Date of Patent: Apr. 17, 2018

(54) IMMOBILISED-BEAD IMMUNOMULTIPLEX ASSAY

(75) Inventors: Stephen Kilfeather, Newcastle Upon Tyne (GB); Alberto Taurozzi, Preston (GB); Paul Lehmann, Moreland Hills, OH (US); Elaine Linglee, Newcastle upon Tyne (GB)

(73) Assignee: BIMA LIMITED, North Shields (GB)

( * ) Notice: Subject to any disclaimer, the term of this patent is extended or adjusted under 35 U.S.C. 154(b) by 870 days.

(21) Appl. No.: 13/580,083

(22) PCT Filed: Mar. 4, 2011

(86) PCT No.: PCT/US2011/000309
§ 371 (c)(1),
(2), (4) Date: Feb. 27, 2013

(87) PCT Pub. No.: WO2011/102903
PCT Pub. Date: Aug. 25, 2011

(65) Prior Publication Data
US 2013/0157288 A1 Jun. 20, 2013

Related U.S. Application Data

(60) Provisional application No. 61/305,843, filed on Feb. 18, 2010.

(30) Foreign Application Priority Data

Feb. 18, 2010 (GB) .................................. 1002785.2
Mar. 4, 2010 (GB) .................................. 1003598.8

(51) Int. Cl.
*G01N 33/543* (2006.01)
*G01N 21/75* (2006.01)
(Continued)

(52) U.S. Cl.
CPC ......... *G01N 21/75* (2013.01); *G01N 21/6428* (2013.01); *G01N 33/54306* (2013.01);
(Continued)

(58) Field of Classification Search
CPC ......... G01N 21/6428; G01N 33/54306; G01N 33/54313; G01N 33/54326; G01N 33/582;
(Continued)

(56) References Cited

U.S. PATENT DOCUMENTS 6,544,732 B1 * 4/2003 Chee et al. .................. 435/6.11
7,183,119 B2    2/2007 Qiao
(Continued)

FOREIGN PATENT DOCUMENTS

WO    WO2004044232    5/2004
WO    WO2005085796    9/2005
(Continued)

OTHER PUBLICATIONS

EP Search Report, dated Oct. 28, 2013.
(Continued)

*Primary Examiner* — Chris L Chin
(74) *Attorney, Agent, or Firm* — D. Benjamin Borson; Borson Law Group, PC

(57) ABSTRACT

Embodiments of this invention include image-based systems and methods for detection of one or more analytes. A surface has identifiable analyte-specific capture particle(s) immobilised thereto at any point of an assay, to which different analytes attach due to the affinity of analyte-specific capture molecule(s) linked to the surface of the capture particle(s) for the analyte. Analyte-specific detector molecules with conjugated detection moieties are then attached to the analyte, and a computer assisted, image-based detection system captures images of the capture particles with or without
(Continued)

attached analytes and detector molecules. By using different subsets of analyte-specific capture molecules, each subset having a characteristic identifiable feature; it is now possible to perform capture particle-based, rapid multiplex assays of biological and non-biological analytes without flow. These image-based systems can be used to aid in diagnosis of disease, evaluation of therapy for disease, or laboratory investigation.

21 Claims, 11 Drawing Sheets

(51) Int. Cl.
*G01N 33/58* (2006.01)
*G01N 21/64* (2006.01)
*B01L 3/00* (2006.01)

(52) U.S. Cl.
CPC . *G01N 33/54313* (2013.01); *G01N 33/54326* (2013.01); *G01N 33/582* (2013.01); *B01L 3/5085* (2013.01); *G01N 2021/6441* (2013.01); *G01N 2500/00* (2013.01)

(58) Field of Classification Search
CPC ........ G01N 2021/6441; G01N 2500/00; B01L 3/5085
USPC .......................................... 436/518, 525, 526
See application file for complete search history.

(56) References Cited

U.S. PATENT DOCUMENTS

| 2004/0101191 | A1* | 5/2004 | Seul et al. | 382/151 |
| 2005/0277159 | A1* | 12/2005 | Lehmann et al. | 435/7.5 |
| 2008/0242553 | A1* | 10/2008 | Kayyem | 506/9 |

FOREIGN PATENT DOCUMENTS

| WO | WO2006130347 | 12/2006 |
| WO | WO2007053186 | 5/2007 |
| WO | WO2011014282 | 2/2011 |

OTHER PUBLICATIONS

PCT/US11/00309;Prelim Rpt, Kilfeather.
PCT/US11/00309; SchReport, Kilfeather.
PCT/US11/00309;Written Op, Kilfeather.

* cited by examiner

A

B

IMMOBILISED-BEAD IMMUNOMULTIPLEX ASSAY

CLAIM OF PRIORITY

This is a United States National Phase of PCT/US2011/00309, filed Feb. 18, 2011 entitled "Immobilised-Bead Immunomultiplex Assay," Stephen Kilfeather, Alberto Taurozzi, Paul Lehmann and Elaine Linglee, inventors, which claims priority to United States Provisional Patent Application No. 61/305,843, filed Feb. 18, 2010, to United Kingdom Provisional Patent Application No. 1002785.2, filed Feb. 18, 2010, and to United Kingdom Provisional Patent Application No. 1003598.8, filed Mar. 4, 2010. Each of the above-identified patent applications is incorporated herein fully by reference.

FIELD OF THE INVENTION

This invention relates to systems and methods for computer-aided image-based detection and analysis of molecules, including biological molecules. Particularly, this invention relates to systems and methods for image-based multiplex analysis of molecules using a plurality of identifiable capture particles ("beads") having spectroscopic features that permit image-based detection and detector molecules having spectroscopic features that permit image-based detection and quantification of molecules.

BACKGROUND

Detection of biological and other analyte molecules is highly useful in diagnosis of medical conditions, evaluation of treatment of medical conditions, for scientific research and other industries. There are currently several approaches to analyte detection. For complex molecules, such as peptides, proteins, RNA, DNA and small molecules, many detection methods rely upon the ability of analyte capture molecules such as specific antibodies or fragments thereof to specifically bind to the analyte of interest. When such analyte-bound capture molecules are made visible (e.g., labelled), the presence of and amount of the analyte can be determined. For example, one form of enzyme-linked immunosorbent assays (ELISAs) is based on the ability of enzyme-conjugated antibodies directed toward the analyte to bind specifically to the analyte of interest. A substrate for the enzyme is then added. Detection of such conjugates, indicating presence of analyte can be accomplished by detecting and quantifying product(s) of enzymatic-derived modification of the substrate. In some of these systems, coloured product(s) are produced, and their detection and quantification can be accomplished using light absorption or emission methods. In certain derivatives of an ELISA, the antibody can be conjugated to a luminescent, fluorescent or radioactive moiety, permitting detection and quantification in the absence of an enzyme.

In other ELISA systems and derivatives of ELISA design, at least two antibodies are used which recognise different epitopes of the analyte (termed "paired"). One of the antibodies takes on the role of capturing the analyte (capturing antibody) and is usually bound to an assay surface. The analyte is brought into contact with the capturing antibody. The second antibody (detection antibody) is then brought into contact with the analyte that is already bound to the capture antibody. The detection antibody is conjugated to a molecule such as an enzyme, or luminescent, fluorescent or radioactive moiety that facilitates detection.

Flow-cytometry-based assays are also currently in use. These assays are based on the detection of labelled particles (including cells) by their passage through a small fluid-filled channel. The appearance of such labelled particles can be detected using laser light and photodetector(s). Such flow-based assays can detect different types of particles based on their size and/or spectroscopic properties, or the presence of a specific marker attached to, or within the particle.

SUMMARY

We have identified a new problem in the field, namely the lack of direct imaging, in the absence of utilisation of flow-based systems, for detection and quantification of a plurality of analytes in solution-derived from biological or non-biological sources. Image-based systems have advantages over prior art methods involving flow cytometry and ELISA methods. We have also supplied solutions to these problems by creating new systems and methods using novel strategies and analytical tools.

Advantages of the Invention

As described further herein, aspects of this invention solve the above and other problems in the art. Compared to flow-based systems using flow-cytometers, aspects of this invention avoid the well-known problems associated with the small-diameter tubing, orifices, pumps and problems with clogging. Additionally, aspects of this invention do not require re-mobilisation of the beads—a step well known to introduce variability in conventional cytometer-based assays. Similarly, it is well known that in conventional cytometer-based assays, the products produced (e.g., individual "beads") are typically lost after an assay run has been completed, making it difficult or impossible to re-run the assay. Because in assays of this invention, analytes, their capture particles and their detection moieties can remain immobilised on a detection surface, the plates can be re-imaged and re-analyzed numerous times. Similarly, because the positions of each element (e.g., capture particle-analyte-detection molecule complex) remain immobilised on the detection surface, the relationships between elements in a composite image do not change.

Aspects of the Invention

Aspects of this invention include systems and methods for image-based analysis of identifiable analyte-specific capture particles, or "beads" that are linked to analyte-specific capture molecules which may be bound to the analyte and detected using image-based instruments.

From this point herein, the term "capture particle" can be used interchangeably with the terms "bead", "beads", "particle", "micro-particle", "nano-particle" and "macro-particle".

In some aspects, a detection plane is prepared by immobilising identifiable capture particles to the surface within the detection plane prior to imaging. In some aspects, the surface within the detection plane is a multi-well plate, which may have 3, 6, 12, 24, 48, 96, or up to 360-well or more wells.

In other aspects, a detection matrix is produced in which a plurality of identifiable capture particles with attached analytes are immobilised prior to imaging.

In other aspects, a plurality of subsets of analyte-specific capture particles is used, each subset having a capture particle identification parameter that distinguishes that subset of particles from other subsets of particles. In some embodiments, detection properties include bead size, composition, luminescence, colour, combinations of colour, electromagnetic emission profile or electromagnetic emission intensity.

In some embodiments, analyte-specific capture particles can be distinguished based on their size or shape. Spherical analyte-specific capture particles can have diameters of 1 μm, 5 μm, 10 μm, 15 μm, 20 μm or of any other size. In other embodiments, analyte-specific capture particles need not be spherical. Rather, they can be cylindrical, conical, elliptical, ribbon-like, ovoid, spiral, amoeba-like, tube-like, or flat sided. Flat-sided analyte-specific capture particles can have four or more numbers of sides.

In other aspects, beads can be identified based on physical features of their surfaces. Therefore in different embodiments, beads can be flat, curved, rough, smooth, dendritic or undulating.

In further aspects, analyte-specific capture particles can be identified based on their chemical composition. Thus, analyte-specific capture particles may be made of polymers, composites, inorganic materials, or natural products.

In some of these aspects an analyte-specific capture particles may emit electromagnetic radiation in the range of ultraviolet to infrared.

In embodiments in which beads are polymers, the polymer can be chosen from the group consisting of polypropylene, polyethylene, polyacetylene, polypyrrole, and conducting polymers.

In embodiments in which beads are composites, the composite can be chosen from the group consisting of glass fibre composites, and carbon fibre composites.

In embodiments in which capture particles are natural products, the natural product can be chosen from the group consisting of silk, gelatin, agarose gels, wax, rubber, and resins.

In other embodiments, analyte specific capture particles can be imaged after their being drawn to a multi-well plate by way of positive pressure, positive pressure-based filtration, negative pressure, gravity, electrostatic or by freezing the solution.

In additional embodiments analyte-specific capture particles can have cores of material sensitive to magnetic forces. In some of these embodiments, analyte-specific capture particles can have iron core or coating.

In additional aspects, an analyte-specific capture particle is a biological cell. The analyte in this case may be a cell surface or intracellular component or product of the cell.

In other aspects, analyte-specific capture particles have analyte-specific capture molecules attached thereto. In some embodiments, analyte-specific capture molecules may include antibodies (monoclonal or polyclonal), or Fab fragments of antibodies, analyte-specific receptors or fragments thereof.

In some aspects, analyte-specific capture molecules can be attached to analyte-specific capture particles using moieties that facilitate conjugation of capture molecules to capture particles.

In some embodiments, such moieties can be selected from the group consisting of carbonyls, amines, thiols, imines, and vinyls.

In alternative embodiments, an analyte-specific capture molecule can be any biological or synthetic molecule to which the target analyte shows affinity at a concentration of 10 millimolar or less. In certain of these embodiments, these molecules can include antibodies, antibody fragments (Fab regions), receptors or receptor fragments, substrates of the target analyte, vitamins or inorganic molecules and derivatives thereof.

Analyte-specific capture particles with analyte-specific capture molecules can be conveniently manufactured prior to immobilisation to a detection plane substrate. In that fashion, subsets of analyte-specific capture particles have respective specific analyte-specific capture molecules.

Analyte-specific detector molecules can be attached to a chromophore, fluorophore or luminescent moiety.

Some aspects include use of magnetism to draw analyte-specific capture particles to a detection plane surface.

Analyte-specific capture particles can be immobilised to a detection plane surface using electrostatic force, or biological or chemical means.

A capture particle immobilisation subsystem can be employed wherein the capture particles, with or without analyte and detector particles attached, have been brought within the imaging plane prior to immobilisation. The capture particle immobilisation subsystem could include tethering molecules, physical forces, or incorporation within a matrix.

In some embodiments, tethering immobilisation of analyte-specific capture particles to a detection plane surface can be accomplished using means chosen from the group consisting of antibody-antigen interaction, covalent attachment, ionic interaction, hydrogen bonding and Van der Waals interaction.

In some embodiments, force-based immobilisation of analyte-specific capture particles to a detection plane surface can be accomplished using means chosen from magnetism, electrostatic forces, creation of positive or negative pressure or gravity.

In some embodiments, incorporation within a matrix immobilisation of analyte-specific capture particles to a detection plane surface can be accomplished using liquid-derived solid matrices, examples of which are resins, waxes, glues, adhesives or gels. The embodiment can include partially solid matrices sufficient to maintain immobilisation of the capture particles, examples of which include resins, waxes, glues, adhesives or gels.

In some of these embodiments, once a detection plane surface has had analyte-specific capture particles immobilised thereto, a sample containing an analyte of interest is added.

In some embodiments the sample containing the analyte of interest can be added to non-immobilised capture particles, followed by detector molecules. Subsequently capture particles with or without an analyte-detector molecule complex bound to their surface can be immobilised to the surface prior to being placed within an image capture system.

In some embodiments, an analyte of interest may be inorganic, biological or synthetic.

A sample may be obtained from an in vivo or an in vitro experiment.

In certain embodiments, analyte(s) can be used to simultaneously screen for any disease(s), diagnose any disease(s), ascertain severity of any disease(s) and/or measure patient response(s) to any treatment(s).

In certain embodiments analyte(s) can be used to simultaneously screen for any non-human animal or plant disease(s), diagnose any disease(s), ascertain severity of any disease(s) and/or measure animal response(s) to any treatment(s).

In certain embodiments analyte(s) can be detected in samples derived from the following industries and associated industries: private and public health services, veterinary, cosmetic, agriculture, food production, water, pharmaceutical, diagnostic, biological laboratory, horticultural, fishery, marine crop, government agencies, forensic, security, toxicological, environmental, biotechnology, institutes of higher education (e.g. colleges and universities), contract research organisations, central laboratory testing organisations, brewing, wine and spirits, bio-fuel, textile, chemical, paper, preservation, healthcare (e.g. medical equipment, biomaterials and prosthetics).

In general, it can be useful to provide a sample in fluid form, including aqueous media. After incubation of the sample with capture particles conjugated to capture molecules, some analytes can bind specifically to their respective analyte-specific capture molecules, whereas other analytes remain in solution. After rinsing the detection surface and/or free capture particles, unbound analytes are removed, leaving analyte(s) bound to their respective analyte-specific capture molecule(s).

Then, analyte-specific detector molecule(s) with conjugated fluorophore, luminescent moiety, or chromophore can be added. After the analyte-specific detector molecule(s) is added, the micro-well plate is then placed within an image capture system.

In certain aspects, the image capture system can include a multi-well plate holder compatible with at least one type of well-plate, and a plate having at least one well.

In certain embodiments, the image capture system also includes at least one lens, at least one camera, or alternative image capturing device, such as a charge-coupled detector (CCD), at least one light source, at least one light filter.

In some embodiments, a multi-well plate can be moved with respect to an image capturing device.

In other embodiments, a multi-well plate may be held stationary and an image capturing device may be moved with respect to the plate. In these embodiments, it is not necessary to immobilise the analyte specific capture particle, as the particle will not be subject to forces that would tend to move the particle within the well of the multi-well plate.

During analysis, an analyte specific capture particle bound to an analyte bound to an analyte detection moiety is identified and its location in the well is stored in a memory device.

In some embodiments, a plurality of analyte specific capture particles may be held in suspension or in a matrix, in which not all of the particles are in the same detection plane. In some of these embodiments, an imaging step includes storing the position of one or more particles in three-dimensions.

In other embodiments, a detection system also includes a computer, operably linked to the image capture system.

In some of these embodiments, a computer has instructions for carrying out one or more of the following steps:
(1) a Capture Particle Distinguishing Step, comprising:
  (a) movement of a multi-well plate holder;
  (b) lens focusing;
  (c) image capture using at least one filter;
  (d) creating a "ring" or "annulus" around the circumference of any image of the particle; or generating an "outline" of the perimeter of any image of the particle.
  (d) storing in memory, location of one or more particles in at least two dimensions within a well;
  (e) identification and classification of a pooled population of subsets of capture particles;
(2) a Recording Step, comprising one or more steps of:
  (a) recalling from memory the location of a particle imaged in a Capture Particle Distinguishing step;
  (b) use of a filter different from the filter used in step a Capture Particle Distinguishing step;
  (c) re-imaging of the capture particle(s), incorporated or not into a fluorescent, luminescent or coloured complex to measure the intensity of fluorescence at a wavelength specific for the detection molecule;
(3) an Analysis Step, comprising:
  (a) use of said measurement recorded in step (2) to determine the presence and/or quantity of at least one analyte using interpolation within a "standard curve" for said analyte generated using the detection system.

In certain of these aspects, a computer assists in imaging of additional fields of view within a well of a multi-well plate until sufficient analyte-specific capture particles of each subset are imaged prior to imaging of other wells in a multi-well plate. This process can be carried out using the following steps:
(1) movement of the plate holder to another well or portion of the same well;
(2) re-focusing of the lens, followed by repeating the Capture Particle Distinguishing Step and Recording Step above on the additional fields of view.

In alternative embodiments, an imaging system is moved between wells and the plate is held stationary.

In still further aspects, a computer assists in predicting luminescence or fluorescence values under conditions where detector molecule luminescence or fluorescence exceeds the limit of detection ("white out"). This can be accomplished by repeating the Recording Step above at lower luminescence or fluorescence detection sensitivity, followed by calculation of the predicted luminescence or fluorescence that would have been obtained at a higher luminescence or fluorescence detection sensitivity at which "white-out" was observed. The predicted value can then be used in the Analysis Step above.

In yet further aspects a computer assists in recognising and excluding capture particles and/or luminescent or fluorescent complexes that are in sufficiently close proximity to interfere with other detection molecule's luminescence or fluorescence.

In still further aspects, a computer assists in recognising objects that are not capture particles, including debris, but have been imaged in a Capture Particle Distinguishing Step and Recording Step above, and assists in their exclusion from incorporation into the Analysis Step above.

Some aspects include a non-flow-based multi-analyte detection system for use with a computer, incorporating interrogation of the existence and extent of a fluorescent complex formation on analyte-specific capture particles previously exposed to a sample in which the presence and/or quantity of at least one analyte needs to be determined, and immobilised to a substratum in an image detection plane comprising:
  (1) said analyte-specific capture particle having the following properties:
    (i) at least one capture particle identification parameter that distinguishes the said capture particles of one subset from those of another,
    (ii) analyte-capturing molecule specific for at least one analyte and attached to the surface of the said capture particle;
  (2) an analyte, and
  (3) one or more analyte-specific fluorescent detector molecules,
wherein said detection system further comprises:
  (a) a multiwell plate holder compatible with at least one type of well-plate,
  (b) a multiwell plate of at least one well,
  (c) at least one said fluorescent complex component, (d) at least one lens,
(e) a camera or alternative image capture device,
(f) at least one light source, and
(g) at least one light filter; said camera being operably linked a computer.

Other aspects include systems as described above wherein said computer has the capacity to assist at any point in the following steps:
(1) a Capture Particle Distinguishing Step, comprising:
   (a) moving said multi-well plate holder,
   (b) focusing said lens,
   (c) capturing an image using at least one filter,
   (d) identifying and classifying a pooled population of subsets of said capture particles;
(2) a Recording Step, comprising:
   (a) use of a filter different from those used in the said Capture Particle Distinguishing Step,
   (b) re-imaging said capture particles, incorporated or not into a said fluorescent complex,
   (c) measuring the intensity of fluorescence at a wavelength specific to that of the said detector molecule, said Recording Step measurement being used to determine the presence and/or quantity of at least one analyte in the original said sample;
(3) an Analysis Step, comprising: use of said measurement described in said Recording Step to determine the presence and/or quantity of at least one analyte via interpolation within a standard curve for said analyte generated using the said detection system.

Further aspects include systems as described above where the computer assists in imaging additional fields of view within a multi-well plate well, until sufficient said capture particles of each subset are imaged prior imaging of other wells within said multi-well plate, said assisting comprising moving said well plate holder and re-focusing the said lens or lenses followed by repeating the said Capture Particle Distinguishing Step and Recording Step on the said additional fields of view.

Additional aspects include systems as described above wherein the computer assists in a predicting fluorescence or luminescence values under conditions where said detector molecule fluorescence or luminescence exceeds the limit of detection ('white-out'), comprising:
(a) repeating said Recording Step at lower fluorescence detection sensitivity, followed by
(b) calculating the predicted fluorescence that would have been obtained at the higher fluorescence detection sensitivity at which 'white-out' was observed; wherein said predicted value then being used in the said Analysis Step.

Additional aspects include systems as described above wherein the computer assists in recognising and excluding said capture particles and/or said fluorescent or luminescent complexes that are in close enough proximity to interfere with each other's said detector molecule fluorescence or luminescence.

Further aspects include systems as describe above wherein the computer assists in recognising objects that are not said capture particles, but have been imaged in said Capture Particle Distinguishing Step and Recording Step and assists in their exclusion from incorporation into the said Analysis Step.

Additionally, aspects include systems as described above, wherein said capture particle has a shape chosen from a group consisting of cylindrical, conical, spherical, elliptical, ribbon-like, ovoid, spiral, amoeba-like, tube-like, and flat-sided comprising 4 or more flat sides.

Yet further aspects include systems as described above, wherein the said capture particle emits electromagnetic radiation within the range of ultraviolet to infrared.

Additional aspects include systems as described above, wherein the surface of said capture particle is chosen from the group consisting of flat, curved, rough, smooth, dendritical, and undulating.

Still further aspects include systems as described above, wherein said capture particle is formed from a material chosen from the group consisting of polymers, composites, inorganics, and natural products.

Other aspects include systems as described above, wherein said capture particle is a polymer chosen from the group consisting of polypropylene, polyethylene, polyacetylene, polypyrrole, and conducting polymers.

Additional aspects include systems as described above, wherein said capture particle is a composite chosen from the group consisting of glass fiber composites, and carbon fiber composites.

Further aspects include systems as described above, wherein said capture particle is a natural product chosen from the group consisting of silk, wax, rubber, and resins.

Additional aspects include systems as described above wherein said capture particles have moieties facilitating conjugation of said capture molecules.

In other aspects, systems as described may have a capture particle containing a moiety chosen from the group consisting of carbonyls, amines, thiols, imines, and vinyls.

Still further aspects include systems as described above wherein said capture particles are brought into contact with the surface of the said well plate under electrostatic force.

Other aspects include capture particles have a magnetic core or coating.

Additional aspects include a capture particle having an identification parameter chosen from the group consisting of size, electromagnetic emission profile, and intensity of electromagnetic emission profile.

Still further aspects comprise magnetic means wherein magnetism is used to bring said capture particles in contact with the surface of the said well plate.

Yet additional capture particle immobilisation subsystems include tethering molecules, physical forces or incorporation of said capture particle within a matrix.

In other aspects, tethering immobilisation subsystems of an analyte-specific capture particle to a detection plane surface is accomplished using means chosen from the group consisting of complimentary oligonucleotides, antibody-antigen interaction, covalent attachment, ionic interaction, hydrogen bonding and Van der Waals interaction.

In other aspects, the above said forces of said capture particle immobilisation subsystem of analyte-specific capture particles to a detection plane surface can be accomplished using means chosen from the group consisting of. magnetic forces and/or electrostatic forces and/or positive or negative pressure.

Yet further aspects include systems as described above wherein said capture particle immobilisation subsystem is achieved through incorporation within a matrix using means chosen from the group consisting of liquid-derived solid matrices, resins, glues, adhesives, and gels.

Other aspects include methods for detection of analytes, where capture particle immobilisation is achieved using DNA-based or RNA-based oligonucleotides.

In other aspects, said oligonucleotides are 1-1000 bases in length.

Additional aspects include systems as described above wherein at least two oligonucleotides have a complementary region of greater than or equal to 10 contiguous base pair throughout the entire length of the said oligonucleotides.

Other aspects include methods as described above wherein at least two oligonucleotides have at least one contiguous complementary region throughout the entire length of the said oligonucleotides.

Further aspects include systems as described above wherein said capture molecule conjugated to the said capture particle is a biological or synthetic molecule for which the target analyte shows affinity at a concentration of 10 millimolar or less.

In still additional of the aspects above, said capture molecule comprises: an antibody, an antibody fragment, a Fab region, a receptor or receptor fragment, a lectin, a substrate of the target analyte, a vitamin, an inorganic molecule, and derivatives thereof.

In some aspects, said detector molecule is a biological or synthetic molecule for which the target analyte has affinity at a concentration of 10 millimolar or less.

In additional of the aspects above, said detector molecule comprises: an antibody, an antibody fragment, a Fab region, a receptor, a receptor fragment, a lectin, a substrate of the target analyte, a vitamin, an inorganic molecule, and derivatives thereof, said capture molecule linked to a chromophore, fluorophore, luminescent moiety or fluorescent moiety.

Other aspects of systems include a detector molecule with a chromophore and/or fluorophore property is used in the same assay as a fluorescent particle-attached detector molecule.

In further aspects as described above, said analyte is a soluble biological or synthetic molecule.

Additional aspects include methods wherein measurement of said analyte is used to screen for a disease, diagnose a disease, ascertain severity of a disease in any animal or plant and/or measure human patient, nonhuman patient or plant response to a treatment.

In some of the above aspects, measurement of said analyte is conducted on a sample derived from an in vitro or in vivo study.

Other aspects include systems for image-based detection of analytes as described herein.

Yet further aspects include methods for detecting and/or quantifying the amount of an analyte in a sample comprising use of a system of any of the above aspects.

BRIEF DESCRIPTION OF THE FIGURES

This invention is described with reference to specific embodiments thereof. Other aspects of the invention can be appreciated with reference to the Figures in which:

FIG. 4 is a series of photographs of images of an embodiment of this invention demonstrating the immobilisation of capture particles within a gel matrix as depicted in FIG. 1.

FIG. 5A is a series of photographic images taken of the immobilised capture particles of this invention demonstrating fluorescence. FIG. 5B is a series of photographic images taken of an embodiment of this invention, wherein the detection of fluorescence of the immobilised capture particles corresponds to the capture particles above in FIG. 5A.

DETAILED DESCRIPTION

Figure 1:
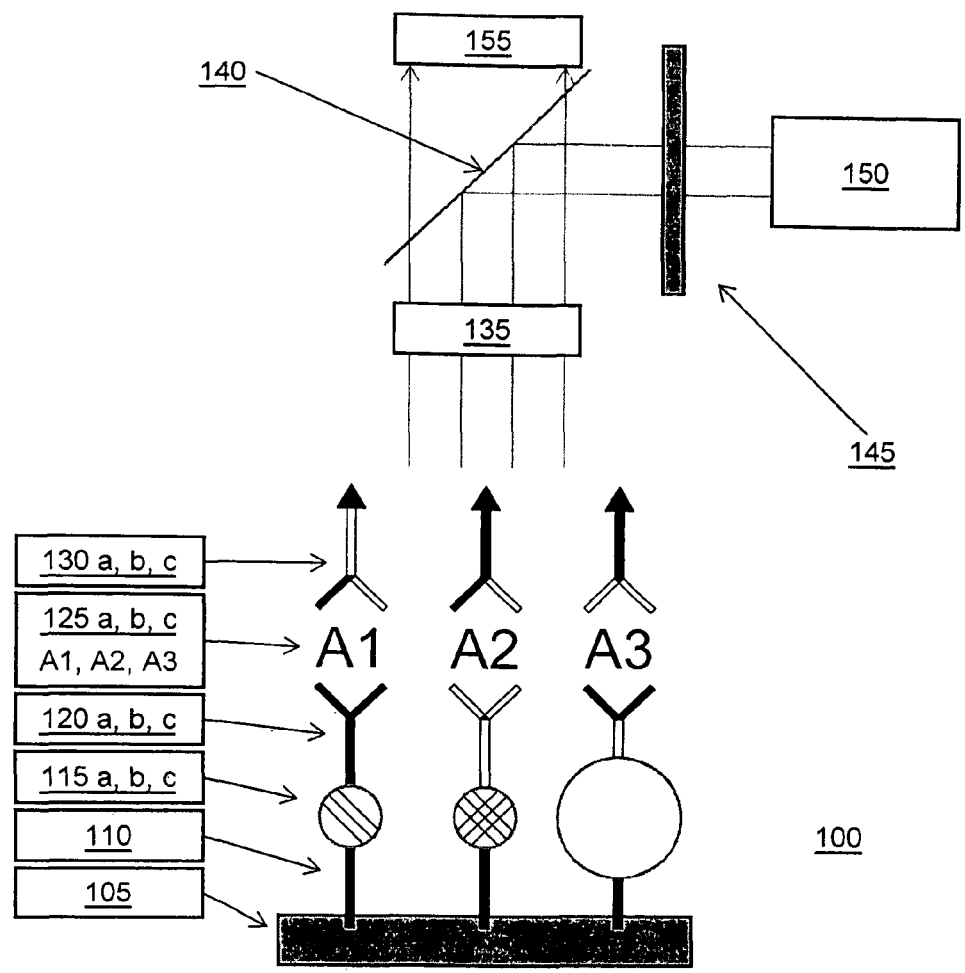
FIG. 1 is a schematic diagram of an embodiment of a detection system of this invention.

This invention provides solutions to existing and new problems in the field of analyte detection. There are several disadvantages of flow-based multiplex assays. Flow-based analyte measurement systems involve sampling of each well in a multi-well plate by removal of fluid in which beads for analysis are contained. The beads are then examined individually, in series, as they pass through laser light, and the emission of light from the particles is recorded individually and in series.

Flow-based systems often require extensive 'warm up' of the fluidics system, since they are often pressure-based fluidics having a narrow working temperature range. The routine 'warm-up' and pre-cleaning schedules required before sample analysis incur lengthy additional time. An imaging system of this invention does not require a period of 'warm-up'. Further, because particles are analysed in series, fluctuations in a flow-system's temperature during a run can adversely affect the results. Such adverse effects include increased noise.

Flow-based systems are prone to pathogen growth including bacterial and fungal contamination and therefore need regular cleaning with fluids that need to be removed from the system prior to use of the machine. An imaging system is never in direct contact with the sample wells or involves fluidics, and therefore is not susceptible to pathogen contamination.

The series examination of beads incurs greater time for examination compared to simultaneous examination in image analysis.

The relatively long time required for series-based examination of individual beads in flow-based systems exposes the well awaiting sampling to light and therefore bleaching of the beads to be sampled. This bleaching results in loss of the integrity of bead identification.

The additional time required in flow-based sample and examination leads to sedimentation of beads in un-sampled wells and loss of bead access to the sampling probe. Circumvention of this problem is only achievable by halting the process of sampling and analysis to allow removal of the plate and re-suspension of the beads within affected wells.

Flow-based systems by the nature of common probe used to sample each well are prone to internal carryover of beads from one sampling and examination round to another. This is reduced by an internal wash between each sample to be analysed and therefore incurs additional time. Additionally, flow-based systems are prone to external bead carryover from one well to subsequent wells by transport of beads on the exterior of the probe. Without manual washing of the probe between each sampling, beads are transplanted from one well to the next. This is very evident when beads carrying high levels of fluorescence are transferred into adjacent wells with beads of low levels of fluorescence, resulting in skewing of the data means.

The absence of probe and fluidics in an imaging-based system of this invention completely avoids these problems of increased examination time and unidentifiable inaccuracies in analysis.

The speed of examination in flow-based systems is dependent upon the concentration of beads in the sample fluid. The speed of imaging systems of this invention within a single image capture is not dependent upon the concentration of beads imaged.

Flow-based systems also suffer from the problem of "carry over" of beads from one well into another well. Carry over may produce spurious results, especially if a particle that is carried over has a higher signal intensity than the population of particles in the sample next to be analysed. This problem is completely avoided by imaging based systems of this invention.

Reanalysis of beads is not possible in flow-based systems as beads from different wells are mixed in the waste fluid of the flow-based system. Whereas in an imaging based system of this invention, the assay plate and beads therein can be retained indefinitely for reanalysis.

Flow-based systems do not provide a visual record of the bead analysis for verification of the analysis. Imaging based systems of this invention provide a permanent visible image of the analysed beads for confirmation of the validity of the bead examination.

In flow-based systems the sampling probe can experience blockage, the presence of which can only be diagnosed and confirmed by dismantling the sampling section of the equipment. An image-based system of this invention does not involve probe-based examination, and this problem is completely avoided.

Replacement of sampling probes in flow-based systems requires careful re-positioning of the probe to ensure that the probe has correct alignment with the wells to be sampled. Failure to achieve correct alignment often results in the sampling probe collision with the wall of wells to be sampled. This can result in either failure to sample and/or bending of the sampling probe. Together with the necessity to achieve correct sampling probe alignment, the correct sampling probe depth needs to be established. Incorrect depth setting of the sampling probe can result in either insufficient sampling (insufficient probe depth) or insufficient space between probe and well bottom resulting in any of the following: well bottom piercing and loss of sample, bending of probe, prevention of fluid and therefore beads entering probe. All of these problems are avoided with use of imaging based systems of this invention.

Flow-based systems are prone to accumulation of air within the fluidics. This prevents examination of samples and the fluidics system then needs to be purged of air and subsequently re-primed and calibrated; incurring additional time. An image-based system of this invention does not involve fluidics in its operation and therefore does not encounter this problem.

Flow-based systems often use expensive saline solutions containing anti-pathogen compounds. The salt in such solutions often accumulates at points of evaporation within the fluidics leading to malfunction or corrosion of fluidics components. An image-based system of this invention does not involve fluidics in its operation and therefore does not encounter this problem.

Flow-based systems are reliant upon a series of valves and pumps to co-ordinate laminar flow throughout the fluid flow elements. These valves and pumps are susceptible to malfunction. An image-based system of this invention does not involve fluidics in its operation and therefore does not encounter this problem.

Laser alignment for excitation of single beads is critical in flow-based systems for detection and examination of beads in the flow cell. Slight movement of flow-based machines is sufficient to cause misalignment of the laser(s). Realignment of the laser(s) requires the expertise of a trained machine supplier engineer. This contributes to the much higher service contracts associated with flow-based machines than imaging machines. In contrast, imaging-based systems of this invention do not require alignment of lasers with the flow cell. Rather, imaging-based systems of this invention store and recall positions of individual capture particles within the well, and permit repeated detection of identifiable characteristics of the capture particles or the detection moiety (or moieties) attached to the analytes bound to capture particles.

Lasers have a limited lifespan and are very expensive to replace. Failure of the laser is another contributory factor in the very high service contracts associated with flow-based systems. An imaging-based system of this invention does not require expensive laser-based illumination and have more robust and far less expensive light sources for illumination.

Flow-based systems rely upon bead-derived emissions received by a detector. If the detectors also fall out of alignment, this also incurs realignment by a service engineer as described above for lasers. Image-based systems of this invention do not rely upon detectors that require permanently fixed alignment. Thus, these problems are avoided.

From a safety perspective, the close proximity of a dense fluidics network with complex electronic components within a flow-based system provides the potential for fluid contact with the internal live electronic system. This also prevents the capacity to leave the flow-based systems to work independently for the lengthy periods required for priming, warm-up and sampling stages without the presence of an operator. By completely avoiding the need for fluidics elements, imaging-based systems of this invention do not suffer from these potential problems.

Utility

Assays of this invention find use in many industries and can be applied to detect and quantify many analytes.

Detection of Small Molecule Analytes

Many small molecules are indicative of presence or severity of disorders or diseases, and their detection can be useful for diagnosis and evaluation of efficacy of treatment. Below are some categories of disorders and analytes useful for diagnosis, determining severity of disease, and for following progression or treatment. Table 1 below provides examples of specific analytes useful in diagnosis, evaluation

TABLE 1

Analytes Useful in Oncology

| | | |
|---|---|---|
| 6Ckine | B cell-activating factor | Cancer Antigen 15-3 |
| Aldose Reductase | B-Lymphocyte Chemoattractant | Cancer Antigen 19-9 |
| Alpha-Fetoprotein | Bcl-2-like protein 2 | Cancer Antigen 72-4 |
| Amphiregulin | Betacellulin | Carcinoembryonic Antigen |
| Angiogenin | Calprotectin | Cathepsin D |
| Annexin A1 | Cancer Antigen 125 | Cellular Fibronectin |
| Macrophage-Migration Inhibitory Factor | Macrophage-Stimulating Protein Phosphoserine Aminotransferase | Urokinase-type Plasminogen Activator |
| Peroxiredoxin-4 | Tetranectin | Placenta Growth Factor |
| Tenascin-C | Vascular Endothelial Growth Factor C | Thyroglobulin |
| Vascular Endothelial Growth Factor B | Neutrophil Gelatinase-Associated Lipocalin | Vascular Endothelial Growth Factor D |
| Lactoylglutathione lyase | | Ezrin |
| Latency-Associated Peptide of Transforming Growth Factor beta 1 | Nucleoside diphosphate kinase B Osteopontin Osteoprotegerin | Fatty Acid-Binding Protein, adipocyte Fatty Acid-Binding Protein, liver |
| Leptin | Pepsinogen I | Fibroblast Growth Factor basic |
| Macrophage inflammatory protein 3 beta | Stromal cell-derived factor-1 Vascular Endothelial Growth Factor | Matrix Metalloproteinase-2 Prostasin |
| Monokine Induced by Gamma Interferon | Insulin-like Growth Factor-Binding Protein 2 | YKL-40 Interferon-inducible T-cell |
| Vascular Endothelial Growth Factor Receptor 2 | Insulin-like Growth Factor-Binding Protein 3 | alpha chemoattractant Interleukin-2 receptor alpha |
| Transforming Growth Factor alpha | Insulin-like Growth Factor Binding Protein 4 | Interleukin-6 Interleukin-6 receptor subunit beta |
| Hepatocyte Growth Factor | Insulin-like Growth Factor Binding Protein 5 | Monocyte Chemotactic Protein 1 HE4 |
| Hepatocyte Growth Factor receptor | Receptor tyrosine-protein kinase erbB-3 | Heparin-Binding EGF-Like Growth Factor |
| Hepsin | Fibulin-1C | Neuron-Specific Enolase |
| Human Chorionic Gonadotropin beta | Galectin-3 | |
| MHC class I chain-related protein A | Kallikrein 5 Neuropilin-1 | |
| Epiregulin | | |
| Epithelial cell adhesion molecule | | |
| Insulin-like Growth Factor Binding Protein 6 | | |
| Kallikrein-7 | | |

Table 2 below provides some examples of analytes useful for diagnosis, evaluation of severity and therapy for diseases in human beings.

TABLE 2

Some Analytes Useful For Diagnosis of Human Disease

| | | |
|---|---|---|
| Adiponectin | Complement C3 | Immunoglobulin A |
| Alpha-1-Antitrypsin | Creatine Kinase-MB | Immunoglobulin E |
| Alpha-2-Macroglobulin | EN-RAGE | Immunoglobulin M |
| Alpha-Fetoprotein | Endothelin-1 | Insulin |
| Apolipoprotein A-I | Eotaxin-1 | Insulin-like Growth Factor I |
| Apolipoprotein C-III | Epidermal Growth Factor | Intercellular Adhesion Molecule 1 |
| Apolipoprotein H | Epithelial-Derived Neutrophil-Activating Protein 78 | Interferon gamma |
| Apolipoprotein(a) | | Interleukin-1 alpha |
| Beta-2-Microglobulin | Erythropoietin | Interleukin-1 beta |
| Brain-Derived Neurotrophic Factor | Factor VII | Interleukin-1 receptor antagonist |
| | Fatty Acid-Binding Protein, heart | Interleukin-2 |
| C-Reactive Protein | Ferritin | Interleukin-3 |
| Calcitonin | Fibrinogen | Interleukin-4 |
| Cancer Antigen 125 | Fibroblast Growth Factor basic | Interleukin-5 |
| Cancer Antigen 19-9 | Granulocyte Colony-Stimulating Factor | Interleukin-6 |
| Carcinoembryonic Antigen | | Interleukin-7 |
| | Granulocyte-Macrophage Colony-Stimulating Factor | Interleukin-8 |
| CD 40 antigen | | Vascular Cell Adhesion Molecule-1 |
| CD40 Ligand | Growth Hormone | Vascular Endothelial Growth Factor |
| Interleukin-10 | Haptoglobin | von Willebrand Factor |
| Interleukin-12 Subunit p40 | Plasminogen Activator Inhibitor 1 | |
| Interleukin-12 Subunit p70 | Pregnancy-Associated Plasma Protein A | |
| Interleukin-13 | | |
| Interleukin-15 | Prostate-Specific Antigen, Free | |
| Interleukin-16 | Prostatic Acid Phosphatase | |
| Leptin | RANTES | |
| Lymphotactin | Serum Amyloid P-Component | |

TABLE 2-continued

Some Analytes Useful For Diagnosis of Human Disease

| | |
|---|---|
| Macrophage Inflammatory Protein-1 alpha | Serum Glutamic Oxaloacetic Transaminase |
| Macrophage Inflammatory Protein-1 beta | Sex Hormone-Binding Globulin Stem Cell Factor |
| Macrophage-Derived Chemokine | Thrombopoietin |
| Matrix Metalloproteinase-2 | Thyroid-Stimulating Hormone |
| Matrix Metalloproteinase-3 | Thyroxine-Binding Globulin |
| Matrix Metalloproteinase-9 | Tissue Factor |
| Monocyte Chemotactic Protein 1 | Tissue Inhibitor of Metalloproteinases 1 |
| Myeloperoxidase | Tumor Necrosis Factor alpha |
| Myoglobin | Tumor Necrosis Factor beta |
| | Tumor Necrosis Factor Receptor-Like 2 |

Table 3 below provides some examples of analytes useful for diagnosing and evaluating cardiovascular diseases.

TABLE 3

Examples of Analytes Useful for Diagnosing Cardiovascular Diseases

| | |
|---|---|
| Alpha-1-Antitrypsin | Cancer Antigen 125 |
| Apolipoprotein A-I | Carcinoembryonic Antigen |
| Apolipoprotein A-II | CD5 Antigen-like |
| Apolipoprotein B | Complement C3 |
| Apolipoprotein C-I | Connective Tissue Growth Factor |
| Apolipoprotein H | Cortisol |
| Beta-2-Microglobulin | Endothelin-1 |
| Betacellulin | Epidermal Growth Factor Receptor |
| Brain-Derived Neurotrophic Factor | Ferritin |
| Calbindin | Fetuin-A |
| Vitronectin | Serotransferrin |
| Tissue Inhibitor of Metalloproteinases 1 | Serum Amyloid P-Component |
| TNF-Related Apoptosis-Inducing | Tumor Necrosis Factor |

TABLE 3-continued

Examples of Analytes Useful for Diagnosing Cardiovascular Diseases

| | |
|---|---|
| Ligand Receptor 3 | Receptor-Like 2 |
| Follicle-Stimulating Hormone | Kidney Injury Molecule-1 |
| Haptoglobin | Luteinizing Hormone |
| Immunoglobulin A | Macrophage-Derived Chemokine |
| Immunoglobulin M | Macrophage Inflammatory Protein-1 alpha |
| Intercellular Adhesion Molecule 1 | |
| Interleukin-10 | Macrophage Migration Inhibitory Factor |
| Interleukin-11 | |
| Interleukin-17 | Matrix Metalloproteinase-2 |
| Interleukin-6 receptor | Monocyte Chemotactic Protein 2 |
| Interleukin-7 | Peptide YY |
| Sortilin | Prolactin |
| Thrombopoietin | Prostatic Acid Phosphatase |
| Vascular Endothelial Growth Factor | Testosterone, Total |
| | Thyroid-Stimulating Hormone |

Table 4 below lists some examples of analytes useful for detection and evaluation of inflammatory diseases.

TABLE 4

Analytes Useful for Diagnosis and Evaluation of Inflammation

| | | |
|---|---|---|
| Alpha-1-Antitrypsin | Interleukin-5 | Tumor Necrosis Factor beta |
| Alpha-2-Macroglobulin | Interleukin-6 | Tumor Necrosis Factor Receptor-Like 2 |
| Beta-2-Microglobulin | Interleukin-7 | |
| Brain-Derived Neurotrophic Factor | Interleukin-8 | Vascular Cell Adhesion Molecule-1 |
| C-Reactive Protein | Interleukin-10 | |
| Complement C3 | Interleukin-12 Subunit p40 | Vascular Endothelial Growth Factor |
| Eotaxin-1 | Interleukin-12 Subunit p70 | |
| Factor VII | Interleukin-15 | Vitamin D-Binding Protein |
| Ferritin | Interleukin-17 | von Willebrand Factor |
| Fibrinogen | Interleukin-23 | IL-18 |
| Granulocyte-Macrophage Colony-Stimulating Factor | Macrophage Inflammatory Protein-1 alpha | sCD40L EGF |
| Haptoglobin | Macrophage Inflammatory Protein-1 beta | Eotaxin |
| Intercellular Adhesion Molecule 1 | | FGF-β |
| Interferon gamma | Matrix Metalloproteinase-2 | FGF-2 |
| Interleukin-1 alpha | Matrix Metalloproteinase-3 | Fractalkine |
| Interleukin-1 beta | Matrix Metalloproteinase-9 | G-CSF GRO |
| Interleukin-1 receptor antagonist | Monocyte Chemotactic Protein 1 | HGF |
| Interleukin-2 | RANTES | IFNa2 |
| Interleukin-3 | Stem Cell Factor | IFNγ |
| Interleukin-4 | Tissue Inhibitor of Metalloproteinases 1 | IP-10 |
| M-CSF | | KC |
| MIF | Tumor Necrosis Factor alpha | LIF |
| MIG | MCP-1 | LIX |
| MIP-1α | MCP-3/CCL7 | VEGF |
| MIP-1β | MDC/CCL22 | CTACK |
| | TGF α | ICAM-1 |
| | TNF α | SCF |
| | TNF β | SCGF-β |
| | β-NGF | SDF-1α |
| | | TRAIL |
| | | VCAM-1 |

Table 5 below provides some examples of analytes useful for diagnosis and evaluation of metabolic disorders.

TABLE 5

Analytes Useful for Diagnosis and Evaluation of Metabolic Disorders

| | | | | |
|---|---|---|---|---|
| Adiponectin | Complement C3 | Glucagon | Leptin | Progesterone |
| Adrenocorticotropic Hormone | alpha des arg Cortisol | Glucagon-like Peptide 1, total | Luteinizing Hormone | Prolactin Resistin |
| Angiotensin-Converting Enzyme | Follicle-Stimulating Hormone Galanin | Insulin IGF-1 | Pancreatic Polypeptide Peptide YY | Secretin |
| Angiotensinogen | | | | |
| Testosterone, total | | | | |

Table 6 below provides examples of analytes useful for diagnosis and evaulation of kidney diseases.

TABLE 6

Analytes Useful for Diagnosing and Evaluating Kidney Disease

| | | | |
|---|---|---|---|
| Alpha-1-Microglobulin | Connective Tissue | Kidney Injury Molecule-1 | Tamm-Horsfall Urinary Glycoprotein |
| Beta-2-Microglobulin | Growth Factor Creatinine | Microalbumin Neutrophil Gelatinase-Associated Lipocalin | Tissue Inhibitor of Metalloproteinases 1 |
| Calbindin | Cystatin-C | Osteopontin | Trefoil Factor 3 |
| Clusterin | Glutathione S-Transferase alpha | | Vascular Endothelial Growth Factor |

Detection of Enzyme Activity

Many protein modifications exist and enzymes catalyze the addition and removal of such modifications which include, by way of example only, addition or removal of a phosphate group, addition or removal of an acetyl group, an addition or removal of methyl group. Other enzymes cleave a substrate (e.g., protein, carbohydrate, lipid or complexes thereof).

Detection of Phosphorylation (Kinases) and Dephosphorylation (Phorphorylases)

MAP kinases are activated within the protein kinase cascades called "MAPK cascade". Each one consists of three enzymes, MAP kinase, MAP kinase kinase (MKK, MEK, or MAP2K) and MAP kinase kinase kinase (MKKK, MEKK or MAP3K) that are activated in series. A MAP3K that is activated by extracellular stimuli phosphorylates a MAP2K on its serine and threonine residues, and this MAP2K activates a MAP kinase through phosphorylation on its serine and tyrosine residues (Tyr-185 and Thr-183 of ERK2). In vivo and in vitro, phosphorylation of tyrosine precedes phosphorylation of threonine, although phosphorylation of either residue can occur in the absence of the other. Because both tyrosine and threonine phosphorylations are required to activate the MAP kinases, phosphatases that remove phosphate from either site will inactivate them.

The MAP kinase signaling cascade has been well-conserved in evolution from yeast to mammals. Cascades convey information to effectors, coordinate incoming information from other signaling pathways, amplify signals, and allow for a variety of response patterns. They respond to different stimuli by phosphorylating cytoplasmic components and nuclear transcription factors depending on the cellular context. Down-regulation of MAP kinase pathways may occur through dephosphorylation by serine/threonine phosphatases, tyrosine phosphatases, or dual-specificity phosphatases and through feedback inhibitory mechanisms that involve the phosphorylation of upstream kinases. Drugs that selectively down-regulate MAP kinase cascades could prove to be valuable as therapeutic agents in the control of malignant disease. Thus, in some embodiments of this invention, phospho-specific antibodies can recognise phosphorylated epitopes and therefore, presence of kinases or phosphatases can be detected and activities of these enzymes can be measured.

For example, 'IκBα (Phospho-Ser32/36) Monoclonal Antibody (Clone 39A1413) directed against a synthetic peptide containing phosphorylated serine residues corresponding to human IκBα amino acids 32 and 36'. For this example, the phosphorylated target (IκBα (Phospho-Ser32/36)) and the cell clone from which the antibody is derived. The cell clone indicates that only this antibody with this antibody peptide sequence is being referred to, since a clone will only produce antibodies of a single sequence. This antibody (i.e., from clone 39A1413) is available commercially from a number of companies and is therefore a widely known antibody and antibody source for this purpose.

Ubiquitination

Ubiquitin is a small regulatory protein that has been found in almost all tissues (ubiquitously) of eukaryotic organisms. Among other functions, it directs protein recycling by cells. Ubiquitin binds to proteins and labels them for destruction. The ubiquitin tag directs proteins to the proteasome, which is an organelle in the cell that degrades and recycles unneeded proteins. Ubiquitin tags can also direct proteins to other locations in the cell, where they control other protein and cell mechanisms. Ubiquitination is an enzymatic, protein post-translational modification (PTM) process in which the carboxylic acid of the terminal glycine from the di-glycine motif in the activated ubiquitin forms an amide bond to the epsilon amine of the lysine in the modified protein.

The process of marking a protein with ubiquitin (ubiquitylation or ubiquitination) consists of a series of steps:
1. Activation of ubiquitin: Ubiquitin is activated in a two-step reaction by an E1 ubiquitin-activating enzyme in a process requiring ATP as an energy source. The initial step involves production of a ubiquitin-adenylate intermediate. The second step transfers ubiquitin to the E1 active site cysteine residue, with release of AMP. This step results in a thioester linkage between the C-terminal carboxyl group of ubiquitin and the E1 cysteine sulfhydryl group.
2. Transfer of ubiquitin from E1 to the active site cysteine of a ubiquitin-conjugating enzyme E2 via a trans(thio)esterification reaction. Mammalian genomes contain 30-40 UBCs.

The final step of the ubiquitylation cascade creates an isopeptide bond between a lysine of the target protein and the C-terminal glycine of ubiquitin. In general, this step requires the activity of one of the hundreds of E3 ubiquitin-protein ligases (often termed simply ubiquitin ligase). E3 enzymes function as substrate recognition modules of the system and are capable of interaction with both E2 and substrate. In the ubiquitination cascade, E1 can bind with dozens of E2s, which can bind with hundreds of E3s in a hierarchical way. Other ubiquitin-like proteins (ULPs) are also modified via the E1-E2-E3 cascade.

Following addition of a single ubiquitin moiety to a protein substrate (monoubiquitination), further ubiquitin molecules can be added to the first, yielding a polyubiquitin chain. In addition, some substrates are modified by addition of ubiquitin molecules to multiple lysine residues in a process termed multiubiquitination. As discussed, ubiquitin possesses a total of 7 lysine residues. Historically the original type of ubiquitin chains identified were those linked via lysine 48. However, more recent work has uncovered a wide variety of linkages involving all possible lysine residues. In addition, chains assembled on the N-terminus of a ubiquitin molecule ("linear chains"). Work published in 2007 has demonstrated the formation of branched ubiquitin chains containing multiple linkage types. "Atypical" (non-lysine 48-linked) ubiquitin chains have been discussed in a review by Ikeda & Dikic.

The ubiquitination system functions in a wide variety of cellular processes, including: antigen processing, apoptosis, bigenesis of organesses, cell cycle and division, DNA transcription and repair, differentiation and development, immune responses and inflammation, neural and muscular degeneration, morphogenesis of neural networks, modulation of cell surface receptors, ion channels and the secretory pathway, response to stress and extracellular modulators, ribosome biogenesis, and viral infections to name a few.

Ubiquitin can be measured using ubiquitin-specific antibodies, which can be commercially available, and therefore, the level of ubiquination and presence and amount of ubiquination enzymes can be detected and quantified.

EXAMPLES

The following examples are included to illustrate some specific embodiments of this invention. It can be appreciated that persons of ordinary skill in the art can use the disclosures and teachings herein to develop variations of systems, methods and kits that are within the scope of this invention. All such variations are considered to be part of this invention.

Example 1

Image-Based Multiplex Assay I

FIG. 1 depicts a schematic diagram of an embodiment 100 of this invention. Multi-well plate 105 within the detection plane has particle immobilisation subsystem 110 used to immobilise identifiable capture particles 115a, 115b, and 115c thereto. Three identifiable capture particles 115a, 115b, and 115c are shown schematically as circular objects. One (115a on left) is shown with diagonal stripes, to indicate one type of identifiable feature. The particle in the middle (115b) is depicted as cross-hatched, and the particle on the right (115c) is shown of larger size than the others.

It can be appreciated that the different identifiable capture particles 115a, 115b, and 115c can be distinguished on the basis of simple colour, e.g., blue, green, yellow, orange, or can be distinguished on the basis of combination of colours, e.g., blue+green, blue+yellow, green+red, etc. Further, it can be appreciated that identifiable capture particles 115a, 115b, and 115c can be distinguished based on size. Thus, one type of identifiable capture particle may have a small diameter and be blue, whereas another type of identifiable capture particle may have a small diameter and be green. Similarly another type of identifiable capture particle may have a large diameter and be blue. It can be readily appreciated that large numbers of different types of identifiable capture particles can be prepared, each type having one or more uniquely identifying features, making their identification during analysis easy and easily automated.

Example 2

Exemplary Particles Useful for Systems, Methods and Kits

Table 7 below provides some particular examples of such types of particles that can be used with systems, methods and kits of this invention.

TABLE 7

Identifiable Capture Particles

| Capture Particle Types (Based on Detector Colour) | Particle Size (μm) | Particle Colour(s) | Analyte Detector Colour 1 |
| --- | --- | --- | --- |
| 1 | 1 | Blue | red |
| 2 | 1 | Green | red |
| 3 | 1 | Yellow | red |
| 4 | 1 | blue + green | red |
| 5 | 1 | blue + yellow | red |
| 6 | 1 | blue + green + yellow | red |
| 7 | 5 | Blue | red |
| 8 | 5 | Green | red |
| 9 | 5 | Yellow | red |
| 10 | 5 | blue + green | red |
| 11 | 5 | blue + yellow | red |
| 12 | 5 | blue + green + yellow | red |
| 13 | 1 | Ultraviolet | red |

It can be appreciated that every combination of size, shape, and colour of identifiable capture particles is contemplated and is within the scope of this invention. Thus, there may be hundreds or thousands of distinct types of identifiable capture particles.

Attached to each particle is one of several an analyte-specific 'Y-shaped' capture molecules 120a, 120b and 120c. Each of the analyte-specific capture molecules 120a, 120b and 120c has a binding domain (upper portion of the molecule) that is specific for a particular analyte. It can be appreciated that a capture molecule may be an antibody, antibody fragment, ligand for the analyte, or a lectin that binds to the analyte. Thus, the "Y" shape is not intended to indicate that the capture molecule does, in fact, have a "Y" shape, and therefore need not be an antibody.

Also shown in FIG. 1 are three analytes, A1, A2, and A3 (125a, 125b and 125c). These analytes are depicted bound to the analyte-specific capture molecules 120a, 120b and 120c shown immediately below. Three analyte-specific detector molecules 130a, 130b and 130c with conjugated fluorochrome are shown. Each of analyte-specific detector molecules 130a, 130b and 130c are shown bound to its respective analyte A1, A2 and A3.

It can be appreciated that the detector molecules with conjugated fluorochrome can be distinguished from the identifiable capture particle(s). Thus, for the series of types of capture particles shown in Table 1 above, a red fluorochrome attached to an analyte-specific detector molecule can be easily distinguished from the corresponding identifiable capture particle. It can be easily appreciated that other colour schemes can be applied, so that, for example, a capture particle may include a red fluorochrome, and a detection molecule may contain a green fluorochrome. In this way, hundreds or thousands of combinations of identifiable capture particles and their corresponding detection molecules can be prepared and used.

FIG. 1 also shows an imaging lens system to focus the light. A dichroic mirror 140 is also shown, that either: (1) permits passage of light emitted by the identifiable capture particle and fluorochromes to an imaging sensor 155 and an image is captured by a camera or alternative image capture device (not shown), or (2) reflects light from an excitation light source (150 shown on the right side of FIG. 1). Light from the excitation light source passes through a light filter wheel 145 to select the wavelength of light to be shone on the well. Information from the camera is transferred to a computer system (not shown) containing program instructions for image analysis.

In some embodiments a first image is captured through a filter specific for the identifiable capture particle, and a "ring" or "annulus" or "outline" of the perimeter of the capture particle is artificially created around the image of the capture particle. The location of each of the particles in at least two dimensions, and the ring, annulus or outline is stored in memory device of a computer.

In further embodiments, a second image of the same particle is made, but using a filter specific for the detection molecule attached to the analyte (which is attached to the identifiable capture particle). The image system (camera, CCD, etc) is then aligned with the location of the particle and the ring or annulus or outline is used to circumscribe the cross-sectional area of the capture particle. Then, a second image of the particle is captured, but the information contained in the image is related to the number of detection molecules within the annulus or outline.

It can be appreciated that with higher analyte concentration in the sample to be assayed, more analyte molecules will bind to the identifiable capture particle(s) and thus, more detection molecules will be attached to the identifiable capture particle. Thus, the intensity of the signal arising from such a particle will be higher, reflecting an increased concentration of the analyte in the sample.

Example 3

Image-Based Multiplex Assay II

Figure 2:
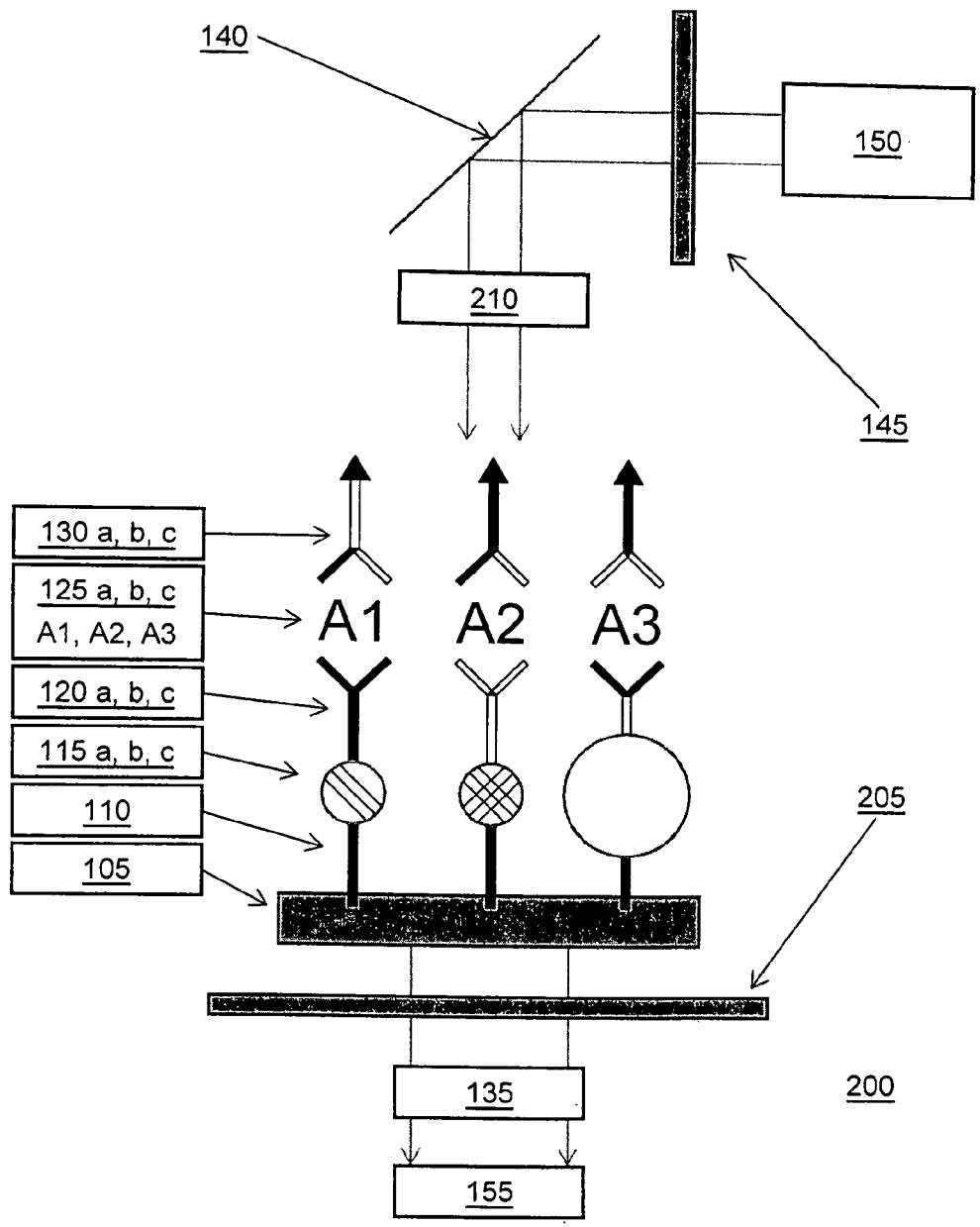
FIG. 2 is a schematic diagram of an alternative embodiment of a detection system of this invention

FIG. 2 depicts an alternative embodiment 200 of an image-based system of this invention. As in FIG. 1 above, a multiwell plate 105, particle immobilisation subsystem 110, identifiable capture particles 115a, 115b and 115c, analyte-specific capture molecules 120a, 120b and 120c, analytes A1, A2, and A3 (125a, 125b and 125c), analyte-specific detector molecules 130a, 130b and 130c with conjugated fluorochrome are shown. In FIG. 2, however, a light filter wheel 205 is positioned below the multiwell plate 105. An imaging lens 135 is depicted below the light filter wheel 205, and an imaging sensor 155 is shown below the imaging lens 135. An excitation focusing lens 210 is positioned above the miltiwell plate 105, and a dichroic mirror 140 projects light passing through a light filter wheel 145 from an excitation light source 150 is shown.

Figure 3:
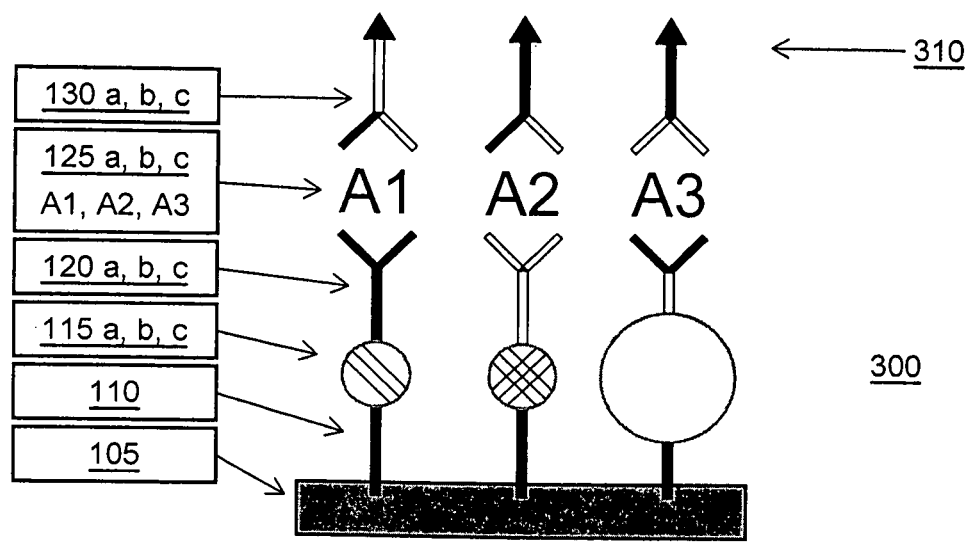
FIG. 3 is a schematic diagram of an alternative embodiment of the immobilisation subsystem of this invention.

FIG. 3 depicts an embodiment 300 of this invention comprising a multiwell plate 105, identifiable capture particles 115a, 115b and 115c, analyte-specific capture molecules 120a, 120b and 120c, analytes A1, A2 and A3 (125a, 125b and 125c), and analyte-specific detector molecules 130a, 130b and 130c with conjugated fluorochrome. In FIG. 3, the identifiable capture particles 115a, 115b and 115c, analyte-specific capture molecules 120a, 120b and 120c, analytes A1, A2 and A3 (125a, 125b and 125c), and analyte-specific detector molecules 130a, 130b and 130c with conjugated fluorochrome are held in position relative to the multiwell plate 105 by way of a particle immobilisation subsystem 310. Such a particle immobliisation subsystem may be a gel (e.g., gelatin or agarose), a glue, a resin, a wax, or an adhesive.

Gels include hybrid sol-gels, colloid gels, transparent oil-water gels, and oil gels, as exemplified below.

Gelatin-derived gels made from gelatin and aqueous and non-aqueous solutions at a range of gelatin concentrations typically but not limited to 0.3 to 10% gelatin solutions. In some embodiments, the concentration may be from 1% to 8%, in other embodiments from about 2% to 6% and in still further embodiments about 3%.

Agarose-type matrix sources include agars (containing agarose and agaropectin) and agarose, particularly, but not limited to low-melting point agarose that can be applied in liquid state at temperatures below 37° C. and therefore protect peptide/protein bonding. Agarose solutions made typically of between 0.5 and 10% (w/v) agarose, but not limited to this range.

Oil gels that are sufficiently clear for imaging. Oil gels including, but not limited to those, made from a Kuraray's SEPTON-4033 thermoplastic rubber or from Kraton 1650 triblock copolymer.

A 'transparent oil-water gel,' or "oil in water emulsion" is a semisolid system that consists mainly of water, oil and an emulsifying agent or agents and that are characterised by a jelly-like consistency and transparency. Many types of these gels are useful.

Lipids include waxes and oils. Low-density oils or oils less dense than capture particles can be used. Here, because the density of capture particles can be higher than that of the oil, the particles tend to sediment on the bottom of a multi-well plate. Oils less dense than capture particles and a higher density than water, such as phthalate-containing compounds are also useful.

Natural and synthetic waxes, particularly, but not limited to those containing a wide variety of long-chain alkanes, esters, polyesters and hydroxy esters of long-chain primary alcohols and fatty acids, particularly, but not limited to transparent, clear or not completely opaque waxes and those termed 'gel-wax', which are essentially transparent on gel formation.

Clear nanotechnology-derived polymer coatings and hybrid ceramic-polymer coatings can also be used as immobilising agents.

The only requirement for an immobilisation subsystem is that it not interfere with the interactions between capture particles, analytes, analyte-specific detection molecules or the components of the multi-well plates.

By use of such a particle immobilisation subsystem, locations of identifiable capture particles can be fixed, and their locations be recalled by the computer system for repeated analysis of features of the identifiable capture particle(s) or of the analyte specific detector molecule with conjugated fluorochrome or luminscent moiety.

In alternative embodiments, identifiable capture particles with analyte and analyte detector molecules can be assayed after a complex of those elements is bound to the bottom of a multiwell plate, via electrostatic interaction, magnetic force, Van der Waals interaction, hydrophobic interaction, chemical attachment, positive or negative pressure (such as vacuum filtration).

In still further embodiments, complexes of identifiable capture particles, analytes, analyte-specific detection molecules with conjugated luminescent moiety or fluorochrome can be assayed with a single image. In these embodiments, a CCD can capture all wavelengths of light emitted by such complexes. Features of identifiable capture particles can then be separated from the analyte-specific detector molecule by computerised analysis of the spectra so captured. Thus, for example, use of a type of identifiable capture particles shown in Table 1, the presence of blue+green+ yellow indicates type 6 particles, and the intensity of a red analyte-specific detector molecule with a "red" fluorochrome is related to the number of analytes on that capture particle.

Another portion of the computer system contains instructions and information for generation of a standard curve and determination of analyte concentrations in the sample.

In additional embodiments, multiple wells of a multi-well plate are analyzed, and images captured and analyzed, and comparisons of information obtained from different wells is compared.

Other embodiments of this invention include methods for using the systems described herein to determine the presence of and amounts of specific analytes. Information obtained using the systems and methods can be used to diagnose diseases, evaluate responses to therapy, and to carry out laboratory research.

It can be appreciated that the descriptions contained herein are for purposes of example only, and that persons of ordinary skill in the analytical arts can use the disclosures and teachings contained herein to produce other variants of these systems and methods without departing from the spirit of this invention.

Example 4

Image-Based Assay

Figure 4A:
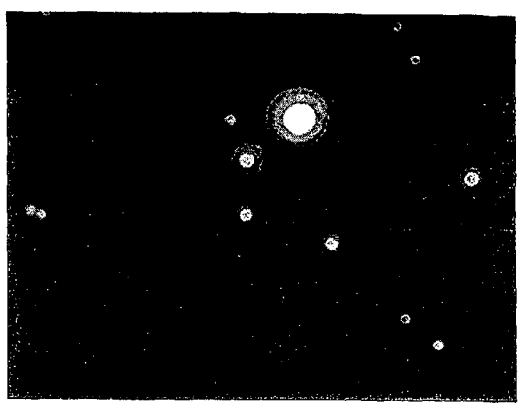
FIG. 4A was captured under conditions when the immobilisation is utilised followed by a washing of the assay well.
Figure 4B:
FIG. 4B was captured under conditions when the immobilisation was not utilised followed by a washing of the assay well.

FIG. 4 is a series of photographic images demonstrating the immobilisation of capture particles within a gel matrix derived from a 3% gelatin solution imaged as depicted in FIG. 1. The image shown in FIG. 4A was captured under conditions when the immobilisation is utilised followed by a washing of the assay well. FIG. 4B is a photographic image that was captured under conditions where the immobilisation was not utilised followed by a washing of the assay well. It can be readily appreciated that immobilisation fixes the locations of capture particles within the well. Also seen in FIG. 4A are particles having three identification features. One particle, the large one, is green. The smallest particles are also green, but because their size is different, they can be readily distinguished from each other. The other particles of intermediate size are blue.

Example 5

Image-Based Assay of Biological Analytes

Figure 5:
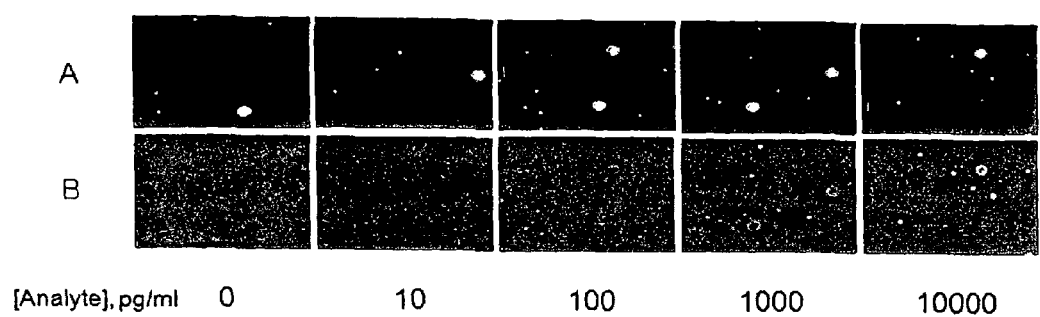
FIG. 5 depicts images taken of an embodiment of this invention, demonstrating measurement of known concentration of three analytes (tumour necrosis alpha (TNFα), interleukin 6 (IL-6) and interleukin 8 (IL-8)) within the same sample as depicted in FIG. 3.

FIG. 5 depicts photographic images taken of measurement of known concentrations of three analytes (tumor necrosis alpha (TNFα) interleukin 6 (IL-6) and interleukin 8 (IL-8)) within the same sample followed by immobilisation of the capture particles within a gel matrix as depicted in FIG. 3. In this case the gel matrix generated was derived from a 3% gelatin solution. FIG. 5A depicts a series of photographic images taken of the immobilised capture particles demonstrating fluorescence characteristic of the different analyte-specific identifiable capture particles. FIG. 5B depicts a series of photographic images of the same fields shown in FIG. 5A but taken through a red filter, showing detection of fluorescence of immobilised capture particles corresponding to the capture particles above in FIG. 5A.

Example 6

Quantification of Image-Based Assay for Biological Analytes I

Figure 6:
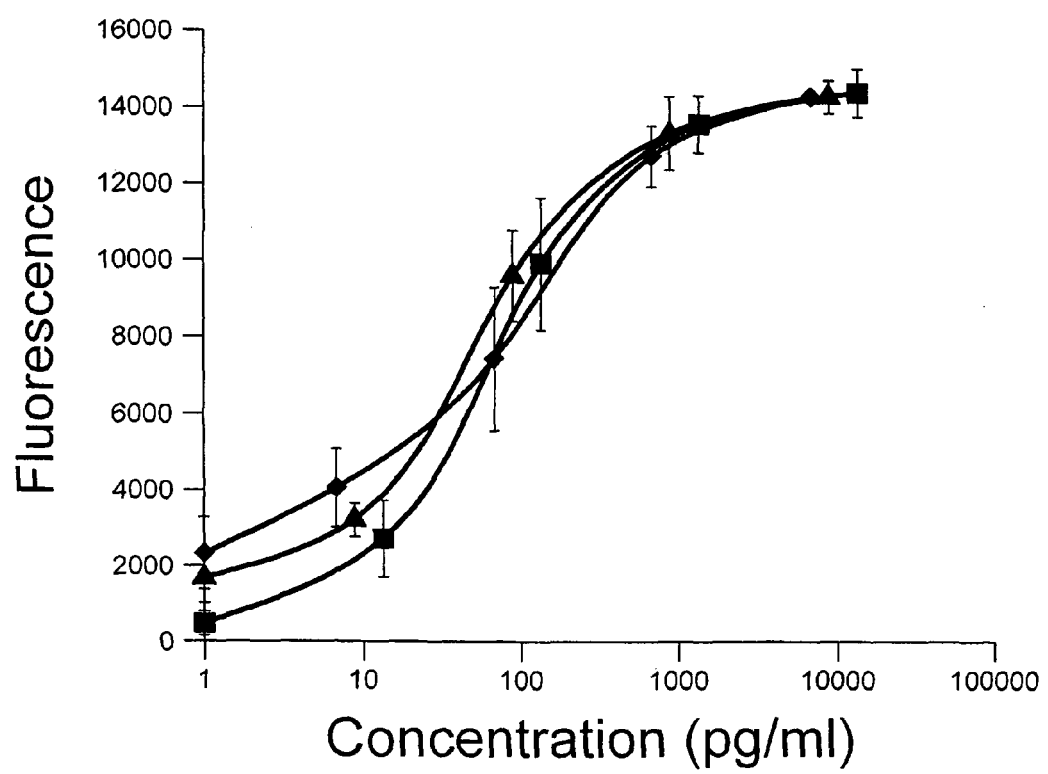
FIG. 6 is a graph of measurement of known concentration of three analytes (tumour necrosis factor alpha (TNFα), interleukin 6 (IL-6) and interleukin 8 (IL-8)) within the same sample of this invention followed by immobilisation of the capture particles within a gel matrix as depicted in FIG. 3. The curves generated for this FIG. 6 were derived from imaging of 5 capture particles for each analyte at each analyte concentration.

FIG. 6 depicts graphs of measurement of known concentration of three analytes (TNFα, IL-6 and IL-8) within the same sample followed by immobilisation of the capture particles within a gel matrix as depicted in FIG. 3. In this case the gel matrix generated was derived from a 3% gelatin solution. The vertical axis represents red fluorescence indicating the amount of fluorochrome associated with the different types of capture particles. The error bars are 95% confidence limits. The horizontal axis represents the concentrations (in pg/ml) of the three analytes. Diamonds represent the amounts of IL-6 (large green particles), filled squares represent the amounts of IL-8 (small UV emitting particles), and triangles represent TNF-alpha (small green capture particles). The curves generated within this figure were derived from imaging of 5 capture particles for each analyte at each analyte concentration.

We conclude from this experiment that imaging based assays of this invention produces highly accurate, very reproducible results.

Example 7

Quantification of Image-Based Assay for Biological Analytes II

Figure 7:
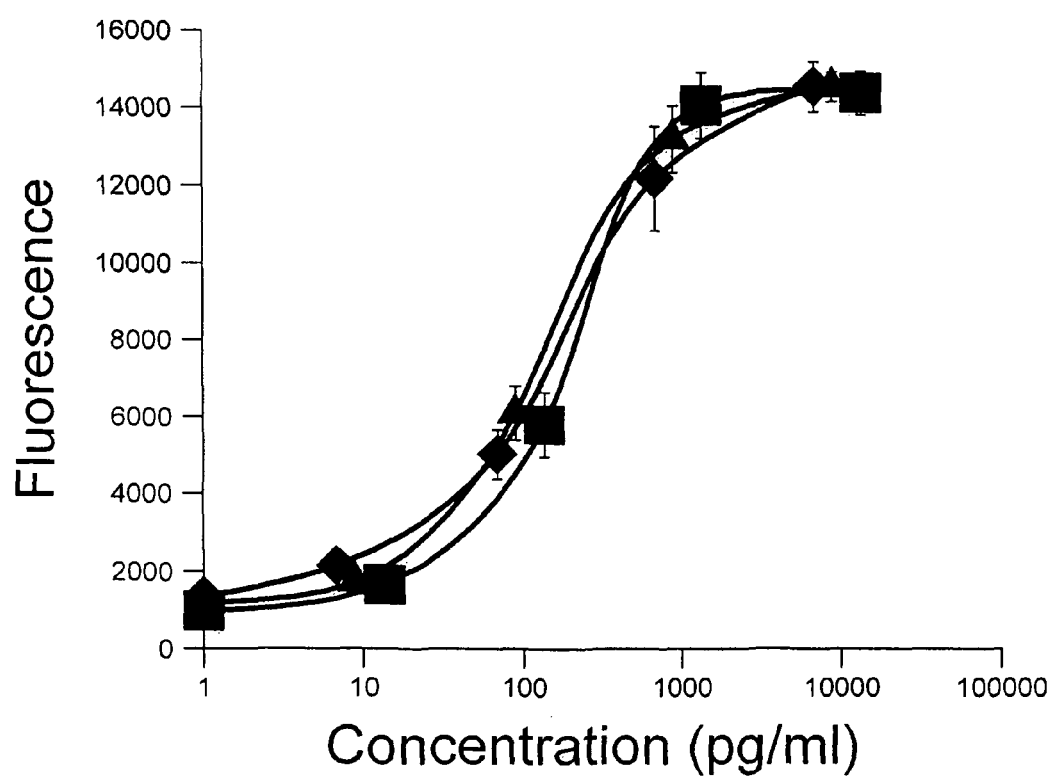
FIG. 7 is a graph of another embodiment of this invention, in known concentration of three analytes (TNFα, IL-6 and IL-8) within the same sample followed by immobilisation of the capture particles within a gel matrix as depicted in FIG. 3. The curves generated within this FIG. 7 were derived from imaging of 20 capture particles for each analyte at the 0 and lowest concentrations of the analyte, and imaging of 5 capture particles for all other analyte concentrations.

FIG. 7 depicts a graph of another embodiment of this invention, showing measurement of known concentration of three analytes (TNFα, IL-6 and IL-8) within the same sample followed by immobilisation of the capture particles within a gel matrix as depicted in FIG. 3. The vertical axis represents intensity of red light emitted by analyte-specific detection molecules with conjugated fluorophore. The horizontal axis represents the concentration of the three analytes (in pg/ml). In this case the gel matrix generated was derived from a 3% gelatin solution. The curves generated within this figure were derived from imaging of 20 capture particles for each analyte at the 0 and lowest values of analyte concentration, and imaging of 5 capture particles for all other analyte concentrations.

Assays of this invention are very sensitive; an analysis of 20 beads has produced an assay having a sensitivity of from 2-3 pg/ml. We conclude from this study that image-based assays of this system produce highly accurate, very reproducible results.

In contrast with the image-based assays of this invention described herein, prior art, flow-based assays can achieve a sensitivity of only about 5-20 pg/ml for an assay of 200 beads.

Thus, the assays of the present invention provide an unprecedented level of sensitivity compared to prior art, flow-based assays. This result is completely unexpected based on the prior art, and represents a highly innovative, advantageous effect compared to the existing flow-based assays.

Figure 8:
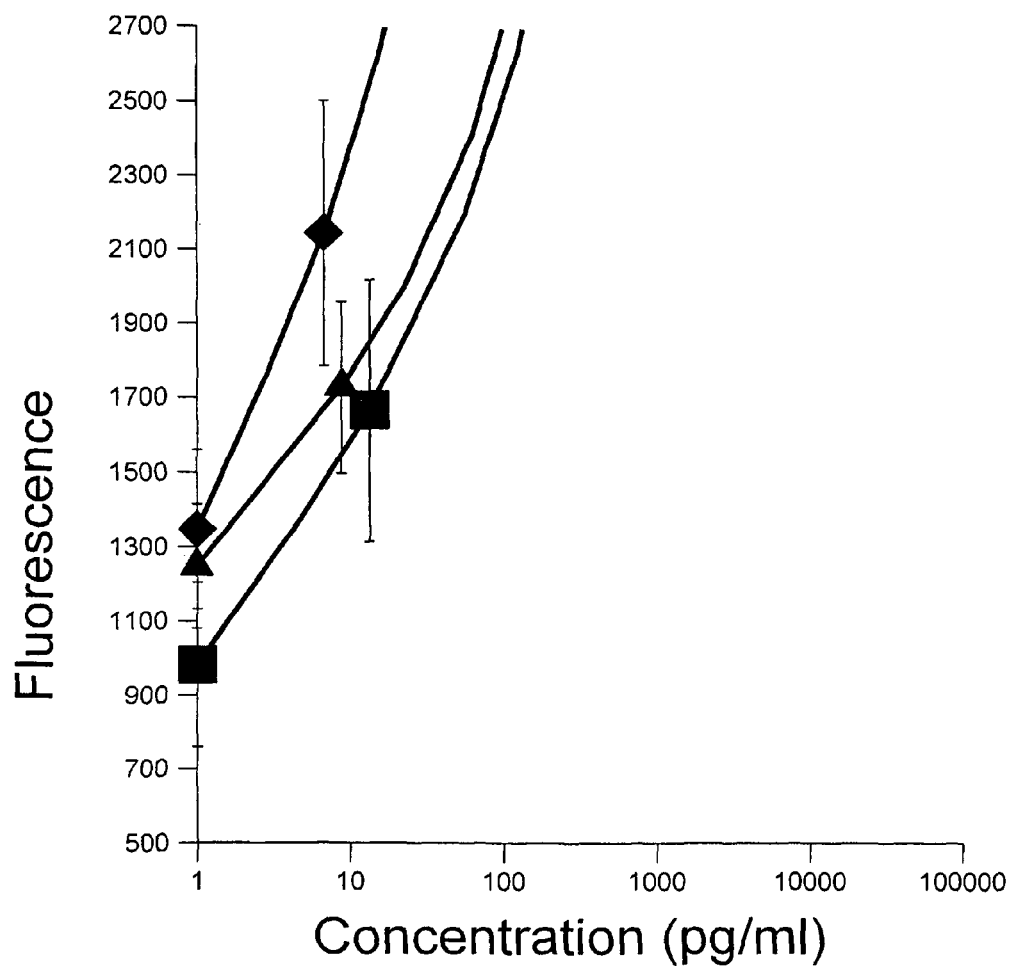
FIG. 8 is an expansion of a section of the graph in FIG. 7 in the region of 0 and the lowest concentration of analyte.

FIG. 8 depicts an expanded portion of the graph shown in FIG. 7 for the region of 0 and lowest concentration of analyte. The horizontal and vertical lines within the graph indicate by interpolation, the limit of detection dictated by the 95% confidence intervals of the 0 concentration values. The interception on the x-axis indicates that for each analyte the limit of detection is in the region of 2-3 pg/ml.

Example 8

Assay for Enzymatic Activity I

In other aspects, this invention includes use of identifiable capture particles with enzyme substrates with a fluorophore conjugated thereto. An enzyme in a solution can cleave such a substrate, liberating the fluoropohore, which can be washed away. Loss of fluorescence or luminescence is indicative of presence and/or activity of an enzyme in the solution.

The identity of the enzyme can be carried out using enzyme specific substrates. Enzyme inhibitors can be used to further identify enzymes in a sample. For example, presence of pepsin in a solution can be inferred by a pepstatin-sensitive loss of fluorescence or luminescence. Similarly, presence of angiotensin converting enzyme (ACE) can be inferred by inhibitor-sensitive loss of detected intensity, wherein the inhibitor is captopril, enalapril, or other ACE-specific inhibitor. Presence of neutral endopeptidase (E.C. 3.4.24.11) can be inferred by thiorphan- or phosphoramidon-sensitivity.

Additionally, presence of collagenase in a solution can be inferred by a collagenase-sensitive loss of fluorescence or luminescence.

In other aspects, this invention includes use of identifiable capture particles with enzyme substrates conjugated thereto. Upon incubation for any given time with a solution that may contain an enzyme capable of modifying said substrate in such a way as to make the substrate identifiable by one or more modification-specific detector molecule conjugated to a fluorophore, chromophore or luminescent moiety. The presence of fluorophore, chromophore or luminescent moiety on said capture particle can be used to calculate the presence and/or activity of said enzyme.

Example 9

Assays for Affinity Calculation

In other aspects, this invention includes the use a ligand or ligand-specific molecule conjugated thereto. A solution containing the ligand-specific molecule or the ligand, either of which is conjugated to a fluorophore, luminescent moiety or chromophore, can bind to the capture particles with the specific ligand or ligand-specific molecule bound to the capture particles respectively. Such a reaction would lead to the capture particles being labelled with the fluorophore, luminescent moiety or chromophore. The extent of labelling at various known concentrations of ligand or ligand-specific molecule in solution can be used to calculate the dissociation constant or association constant and thus calculate the affinity of the ligand-specific molecule for a ligand. Such molecules that can be evaluated in this manner include small or large molecule, peptides, proteins including antibodies.

Example 10

Competitive Assay

In other aspects, this invention includes the use of identifiable capture particles with capture molecules conjugated thereto. A sample containing the analyte to be measured can be incubated with said capture particles before, after or during incubation of said capture particles with a solution containing a known concentration of said analyte with a fluorophore, luminescent moiety or chromophore conjugated thereto (competing labelled analyte). The competing labelled analyte will compete with the unlabelled analyte within the sample for binding to said capture molecules on said capture particles. The extent of fluorophore, luminescent moiety or chromophore present on said labelled analyte on said capture particles can be used to calculate the concentration of the said analyte within said sample.

It can be appreciated that the descriptions of this invention are shown by way of example only, and that other embodiments based on the disclosures and teachings herein can be produced by persons of ordinary skill in the art. All such variations are considered included within the scope of this application and the appended claims.

Example 11

Assay for Enzymatic Activity II

Figure 9:
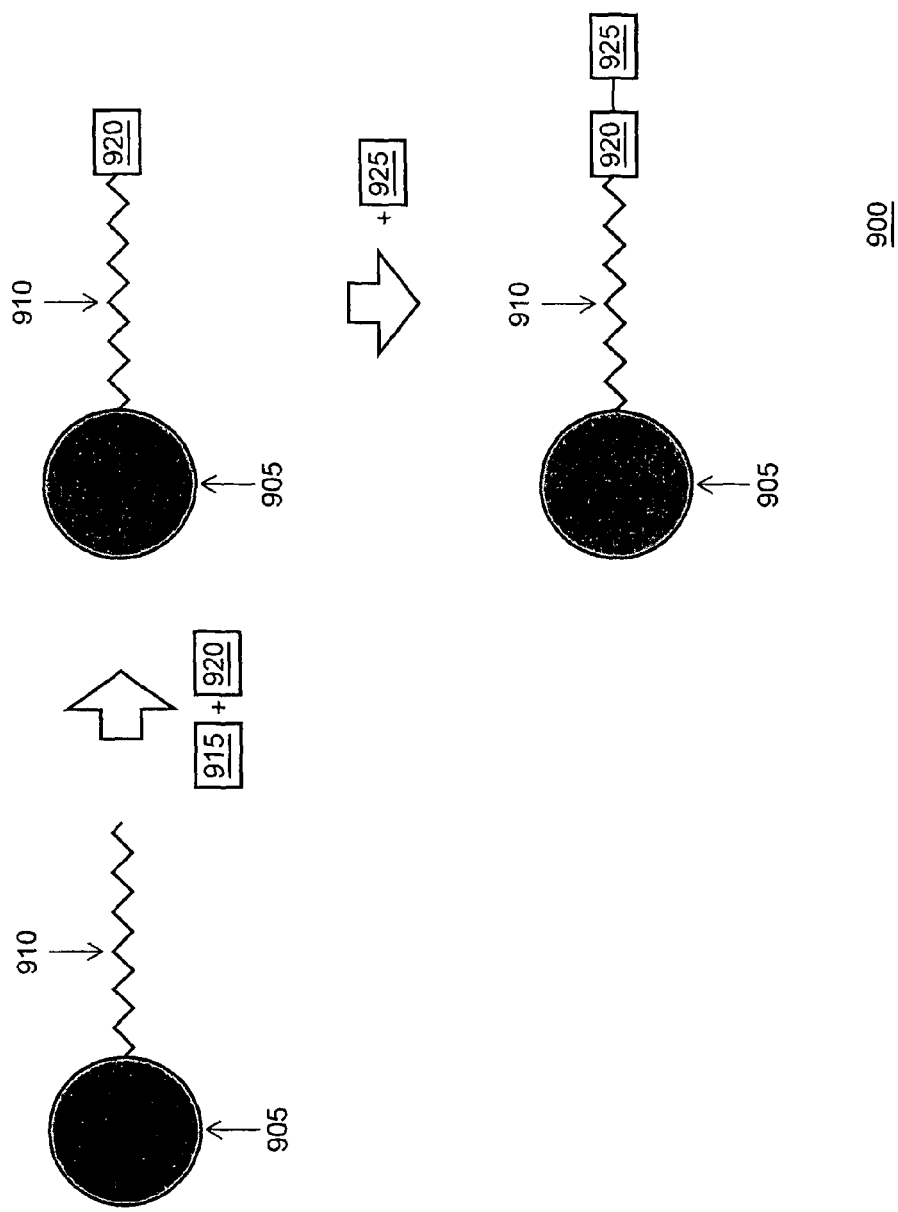
FIG. 9 depicts an assay of this invention for detection and quantification of a phosphorylating enzyme.

FIG. 9 depicts assay 900 of this invention. Capture particle 905 is shown with substrate 910 attached thereto. The analyte in this assay is phosphorylating enzyme 915. In the presence of phosphate 920, phosphorylating enzyme 915 adds a phosphate group 920 to substrate 910, thereby producing a phosphorylated substrate attached to capture particle 905-910-920. A fluorescent-conjugated phosphospecific detection molecule 925 is then added, thereby producing a fluorescent-conjugated complex 905-910-920-925. After removing un-conjugated detector molecule, an image of the immobilised detector molecule is captured and analyzed. From the amount of immobilised fluorescent-conjugated phosphospecific detector molecule present, the amount/activity of enzyme 915 can be determined.

Example 12

Assay for Enzyme Activity III

Figure 10:
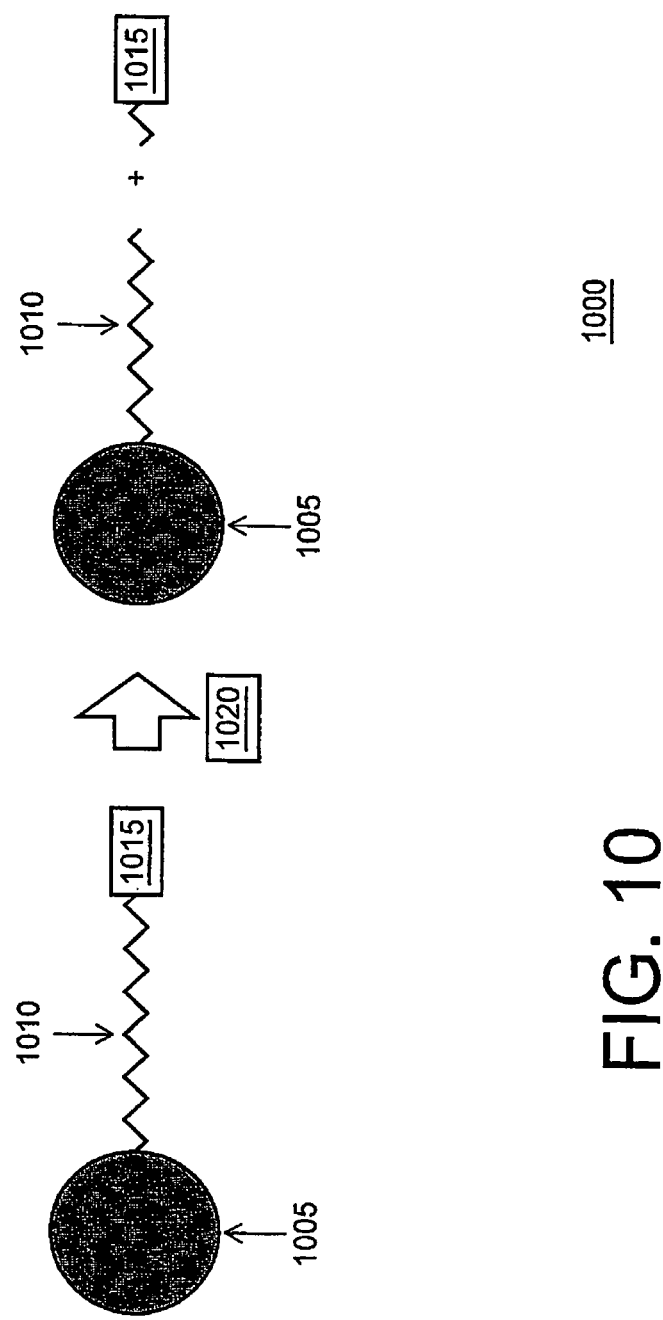
FIG. 10 depicts an assay of this invention for detecting an enzyme that cleaves a substrate with a fluorescent detection molecule attached.

FIG. 10 depicts assay 1000 of this invention. Capture particle 1005 is shown with substrate 1010 with fluorescent tag 1015 attached in series to capture particle 1005 forming complex 1005-1010-1015. The analyte in this assay is enzyme 1020 that can cleave substrate 1010 thereby releasing fluorescent tag 1015. A first image is captured of the detection surface (not shown) with complex 1005-1010-

1015 immobilised thereon. After incubation with enzyme 1020, enzyme 1020 cleaves a portion of substrate 1010, thereby releasing fluorescent tag 1015 and a portion of substrate 1010, which are discarded. A second image is then captured of the detection surface (not shown) of capture particle 1005 with a portion of substrate 1010 attached thereto. The amount of bound detector molecule 1015 is determined and the decrease in intensity of 1015 is indicative of loss of enzyme or its activity.

Example 13

Assay for Enzyme Activity IV

Figure 11:
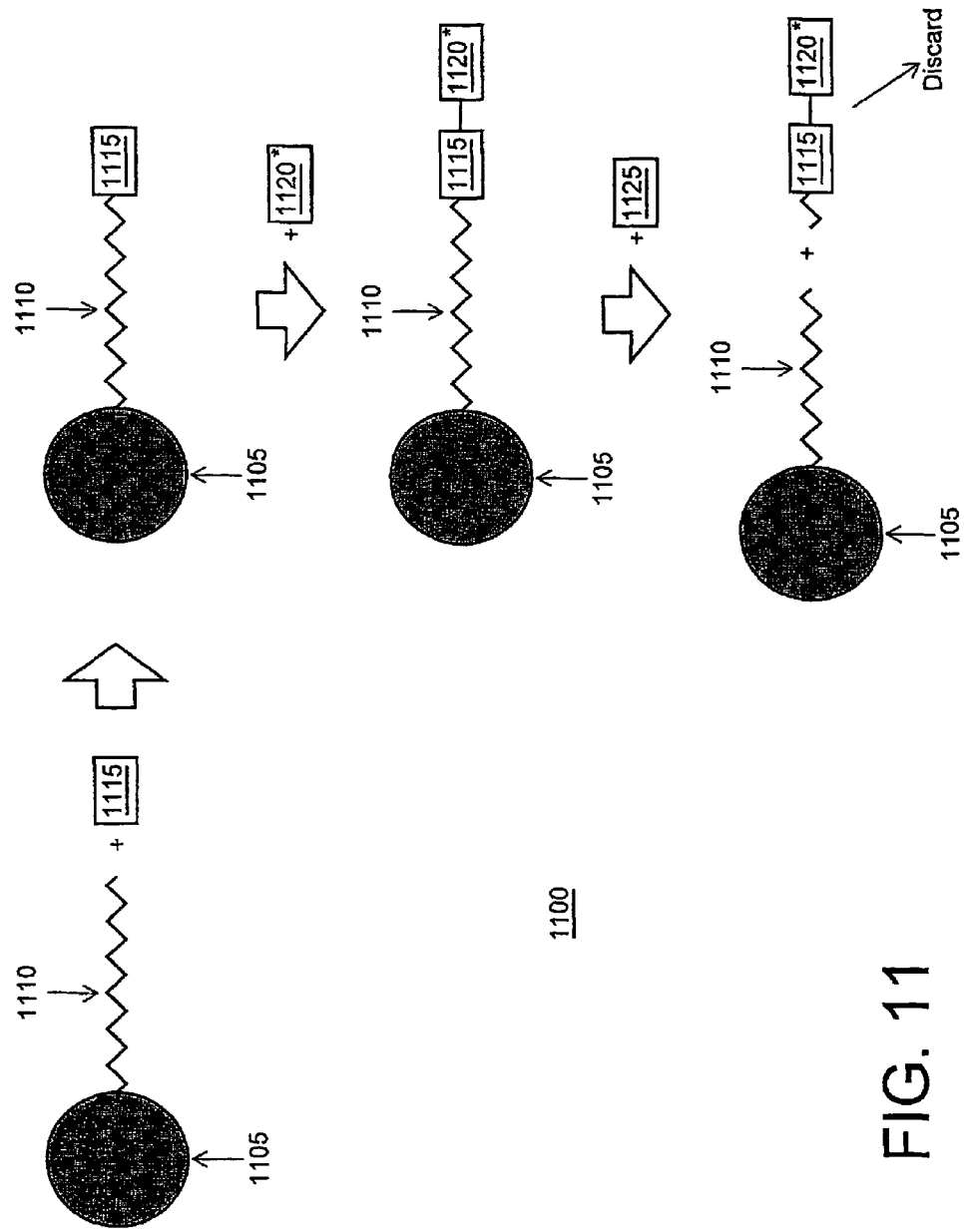
FIG. 11 depicts an assay of this invention for detecting an enzyme that cleaves a substrate with a fluorescent detection molecule attached by way of biotin-streptavidin.

FIG. 11 depicts assay 1100 of this invention. Capture particle 1105 is shown with substrate 1110. Biotin 1115 is then attached to substrate 1110. Then, fluorescently labeled (*) streptavidin 1120 is added, which binds to biotin 1115 thereby forming fluorescently labeled (*) complex 1105-1100-1115-1120. A first image is captured of the detection surface (not shown) with complex 1105-1100-1115-1120 immobilised thereon. Enzyme 1125 is able to cleave substrate 1110, thereby releasing a portion of substrate 1110 with biotin 1115 and labeled (*) streptavidin 1120 attached, which is discarded. A second image is then captured of the detection surface (not shown) of capture particle 1105 with a portion of substrate 1110 attached thereto. The amount of bound detector molecule 1120 is determined and the decrease in intensity of 1020 is indicative of loss of enzyme or its activity.

INDUSTRIAL APPLICABILITY

This invention finds utility in any industrial, medical, or laboratory setting where rapid, accurate detection and quantification of analytes is desired, such as private and public health services, veterinary, cosmetic, agriculture, food production, water, pharmaceutical, diagnostic, biological laboratory, horticultural, fishery, marine crop, government agencies, forensic, security, toxicological, environmental, biotechnology, institutes of higher education (e.g. colleges and universities), contract research organisations, central laboratory testing organisations, brewing, wine and spirits, bio-fuel, textile, chemical, paper, preservation, healthcare (e.g. medical equipment, biomaterials and prosthetics).

What is claimed is:

1. A non-flow based multi-analyte detection system not requiring remobilisation of capture particles, comprising:
    (1) a first type of analyte-specific capture particle, said capture particle having:
        (i) at least one capture particle identification parameter that distinguishes said first type of said analyte-specific capture particle from another type of capture particle,
        (ii) said first type of analyte-specific capture molecule having a binding moiety specific for a first analyte, said binding moiety attached to said capture particle;
    (2) a first type of analyte-specific detector molecules, each of said detector molecules having:
        (i) an analyte-specific binding moiety; and
        (ii) a luminescent moiety having an identification parameter different from that of said first type of capture particle;
    (3) a second type of analyte-specific detector molecules, each of said detector molecules having:
        (i) an analyte-specific binding moiety; and
        (ii) a luminescent moiety having an identification parameter different from that of said first type of capture particle;
    (4) a second type of analyte-specific capture particle, said second type of analyte-specific capture particle having:
        (i) at least one capture particle identification parameter that is different from the capture particle identification parameter of said first type of analyte-specific capture particle;
        (ii) said second type of analyte-specific capture particle having a binding moiety specific for a second analyte, said binding moiety bound to said capture particle,
    (5) a matrix to immobilise in suspension said capture particles with attached analyte and attached detection molecules ("particle complexes") in which not all particles are in the same detection plane; where
    (6) upon binding of a first anlyte to said first type of analyte-specific capture particle, upon binding of said first type of analyte-specific detector molecule to said first analyte bound to said first type of analyte-specific capture molecule, and upon binding of a second analyte to said second type of analyte-specific capture particle, and upon binding of said second type of analyte-specific capture particle binding to a second type of analyte-specific detector molecule to said second analyte bound to said second type of analyte-specific capture molecule, forming:
    a first complex of said first type of analyte-specific detector molecule, said first analyte, and said first type of analyte-specific capture particle: and
    a second complex of said second type of analyte-specific detector molecule, said second analyte, and said second type of analyte-specific capture particle molecule;
    said first complex and said second complex being held in suspension in a matrix, wherein not all said particles are in the same detection plane; and
    (7) a light source, and a camera operably linked to a computer to detect said complexes even if said immobilized complexes are suspended in different detection planes.

2. The system of claim 1, further comprising:
    (a) a multi-well plate holder compatible with at least one type of well-plate, and
    (b) a multi-well plate having at least one well.

3. The system of claim 1, where at least one type of capture particle has a shape selected from the group consisting of cylindrical, conical, spherical, elliptical, ovoid, spiral, or flat-sided comprising 4 or more flat sides.

4. The system of claim 1, where at least one type of said capture particle comprises a material selected from the group consisting of polymers, composites, inorganics, and natural products.

5. The system of claim 1 wherein said capture particles have a magnetically sensitive core or coating.

6. The system of claim 1 where said capture particle identification parameter of at least one of said types of analyte-specific capture particles is selected from the group consisting of size, electromagnetic emission profile, and intensity of electromagnetic emission profile.

7. The system of claim 1 where at least one type of said capture particle is immobilised by a tethering molecule, a physical force, or incorporation of said capture particle in suspension within a matrix, wherein not all of said particles are in the same detection plane.

8. The system of claim 7 where said matrix is selected from the group consisting of liquid-derived solid matrices, resins, glues, adhesives, and gels.

9. The system of claim 1, wherein said capture particle comprises a capture molecule selected from the group consisting of an antibody, antibody fragment, Fab region, receptor or receptor fragment, lectin, substrate of the target analyte, vitamin, an inorganic molecule, and derivatives or combinations thereof.

10. The system of claim 1, wherein said computer has instructions stored therein to perform one of more of the following steps:
(1) a Capture Particle Distinguishing Step, comprising:
  (i) moving a multi-well plate holder,
  (ii) focusing a lens on one or more particles held in suspension in a matrix, wherein not all said particles are in the same detection plane,
  (iii) capturing an image of a capture particle using at least a first filter,
  (iv) identifying and classifying said capture particle;
(2) a Recording Step, comprising:
  (i) re-imaging said capture particle using a second filter different from said first filter, thereby recording of an image of said fluorescent or luminescent complex;
  (ii) measuring the intensity of fluorescence or luminescence characteristic of said detector molecule;
(3) an Analysis Step, wherein:
  (i) said measurement described in said step (2) indicates the presence and/or quantity of at least one analyte.

11. The system of claim 10 where said computer has
(a) instructions stored therein to image an additional field of view within a well of a multi-well plate,
(b) instructions to determine a number of capture particles of each subset to be imaged to achieve a degree of precision of 85% prior imaging of other wells,
(c) instructions to move said well plate holder and refocusing said lens to focus on a particle in a different detection plane followed by repeating said Capture Particle Distinguishing Step and said Recording Step on an additional field of view.

12. The system of claim 10, where in said Analysis step, said computer further comprises instructions stored therein to perform the steps:
(a) predict fluorescence or luminescence values under conditions where said detector molecule fluorescence or luminescence exceeds the limit of detection ('whiteout'), comprising:
(b) repeating said Recording Step at a lower sensitivity of fluorescence or luminescence detection; and
(c) calculating a predicted fluorescence or luminescence value that would have been obtained at the higher sensitivity of fluorescence or luminescence detection at which 'white-out' was observed; wherein said predicted fluorescence or luminescence value then being used indicates the presence and/or quantity of said at least one analyte in said Analysis Step.

13. The system of claim 10 where the computer has instructions stored therein to recognize debris, being objects that are not said capture particles, but have been imaged in said Capture Particle Distinguishing Step and Recording Step and said instructions include steps for exclusion of debris from incorporation into said Analysis Step.

14. A method for detecting and quantifying an analyte, comprising:
providing a system of claim 1;
providing a sample containing the analyte to be measured;
incubating said sample with said capture particle before, during or after incubation of said first capture particle with a solution containing a known concentration of said first analyte, said capture particle having a fluorophore, luminescent moiety or chromophore conjugated thereto;
permitting said labelled analyte to compete with the unlabelled analyte for binding to said capture particle;
adding a first type of detector molecule to said well thereby producing a complex of said capture particle, analyte and detector molecule, said complex being immobilised in suspension by incorporation within a matrix, wherein not all particles are in the same detection plane;
using an image-based detector to determine the amount of fluorophore, luminescent moiety or chromophore present on said complex; and
calculating the amount of said analyte in said sample.

15. The method of claim 14, where said computer contains instructions to distinguish said capture particle from debris, where said debris has a surface selected from the group excluding cylindrical, conical, spherical, elliptical, ovoid, spiral, and flat sided comprising 4 or more flat sides.

16. The method of claim 14, where said analyte is an enzyme and said capture particle has a substrate attached thereto and said enzyme catalyzes an addition reaction to add an additional moiety to or a removal reaction that removes an already existing moiety from said substrate, said detection molecule having a chromophore, fluorophore, or luminescent moiety conjugated thereto binds to said additional moiety or to said existing moiety, further comprising;
(a) incubating said capture particle and substrate with said enzyme and said additional moiety, thereby producing a complex of said capture particle, substrate and said additional moiety; or
(b) incubating said capture particle with said pre-existing moiety with said enzyme; and
(c) incubating said complex obtained in step (a) or step (b) with said detection moiety, and
(d) determining the presence and/or activity of said enzyme by detecting the fluorescence or luminescence on said detection moiety.

17. The method of claim 14, where said analyte is an enzyme and said capture particle having a substrate having a fluorescent tag attached thereto and said fluorescent tag has a fluorescent-conjugated detector molecule comprising a flurophore, chromophore or luminescent moiety, thereby forming a labeled complex, further comprising;
(a) incubating said labeled complex with a solution containing said enzyme; and
(b) determining the presence and/or activity of said enzyme by detecting and quantifying the loss of intensity of said fluorescence.

18. The method of claim 17, where the analyte is selected from the group consisting of small molecule therapeutic agents, peptide therapeutic agents, cell-derived receptors, DNA binding molecules, and antibodies.

19. A kit, comprising:
(1) a multi-well plate;
(2) a subset of capture particles with or without capture molecules pre-conjugated to said capture particles;
(3) a subset of detector molecules with or without pre-conjugation to a fluorophore, luminescent moiety, or chromophore;
(4) a fluorophore, luminescent moiety, or chromophore with a moiety facilitating conjugation or binding to said detector molecule;

(5) reagents for use in the preparation of said multi-well plate, said capture particles, said analytes, said samples, said detector molecules, or said fluorophore, luminescent moiety, or chromophore, for performing the assay;

(6) a matrix used to immobilise in suspension, wherein said capture particles with attached analyte and attached detection molecule ("particle complexes") are suspended within said matrix in which not all particles are in the same detection plane, and (7) a covering for the top of said multi-well plate.

20. A system for image-based analysis of a plurality of analytes, comprising:
- (a) a detection surface having a plurality of types of capture particles thereon, each of said types of capture particles having a uniquely identifiable spectral feature, and each type of said capture particles having at least one analyte-specific capture molecule attached thereto;
- (b) a matrix used to immobilise in suspension, wherein said capture particles with attached analyte and attached detection molecule ("particle complexes") within said matrix in which not all particles are in the same detection plane,
- (c) a plurality of types of analyte-specific detector molecules, each of said plurality of types corresponding to one of said types of analyte-specific capture molecules said capture particles, attached analytes, and attached detector molecules ("particle complexes") being immobilized in suspension by incorporation within said matrix, wherein not all of the particle complexes are in the same detection plane;
- (d) a light source;
- (e) an imaging sensor; and
- (f) a computer having a program stored in a computer memory device having instructions thereon to determine the type and amount of each of said plurality of analytes.

21. A method for image-based analysis of a plurality of analytes, comprising:
- (a) providing a detection surface having a plurality of types of capture particles immobilized thereon, each of said types of capture particles having a uniquely identifiable spectral feature, and each type of said capture particles having at least one analyte-specific capture molecule attached thereto;
- (b) applying a sample containing two or more analytes to said detection surface thereby forming a plurality of analyte-specific capture molecule-analyte complexes ("ASCMAC");
- (c) providing a plurality of types of analyte-specific detection molecules, each type of which comprises a luminescent moiety different from luminescent moieties of other types of detection molecules;
- (d) applying to said ASCMAC, a said plurality of analyte-specific detector molecules with conjugated luminescence moieties attached thereto thereby forming a plurality of ACSMAC-analyte-specific detector molecule complexes ("ASCMASDC");
- (e) immobilising said ASCMASDC in suspension by incorporation within a matrix, wherein not all said particles are in the same detection plane; and
- (f) capturing an image of said ASCMASDC.

* * * * *

UNITED STATES PATENT AND TRADEMARK OFFICE
CERTIFICATE OF CORRECTION

PATENT NO. : 9,945,786 B2
APPLICATION NO. : 13/580083
DATED : April 17, 2018
INVENTOR(S) : Stephen Kilfeather et al.

It is certified that error appears in the above-identified patent and that said Letters Patent is hereby corrected as shown below:

In the Claims

Column 28 Line 20 Claim 1:
Please delete the word "anlyte" and replace it with --analyte--.

Signed and Sealed this
Twenty-fifth Day of September, 2018

Andrei Iancu
*Director of the United States Patent and Trademark Office*